US008352207B2

(12) United States Patent
Tokhtuev et al.

(10) Patent No.: US 8,352,207 B2
(45) Date of Patent: Jan. 8, 2013

(54) METHODS FOR CALIBRATING A FLUOROMETER

(75) Inventors: Eugene Tokhtuev, Duluth, MN (US); Christopher J. Owen, Duluth, MN (US); Soren K. Tryggestad, Brooklyn Park, MN (US); Anna Pilipchenko, Duluth, MN (US)

(73) Assignee: Ecolab USA Inc., St. Paul, MN (US)

( * ) Notice: Subject to any disclaimer, the term of this patent is extended or adjusted under 35 U.S.C. 154(b) by 468 days.

(21) Appl. No.: 12/750,814

(22) Filed: Mar. 31, 2010

(65) Prior Publication Data
US 2011/0246118 A1   Oct. 6, 2011

(51) Int. Cl.
G01N 21/64   (2006.01)
G06F 19/00   (2006.01)
(52) U.S. Cl. ...................................... 702/104
(58) Field of Classification Search ............... 702/104
See application file for complete search history.

(56) References Cited

U.S. PATENT DOCUMENTS

| | | | |
|---|---|---|---|
| 3,988,591 A | 10/1976 | Killer | |
| 4,295,199 A | 10/1981 | Curry et al. | |
| 4,783,314 A | 11/1988 | Hoots et al. | |
| 6,255,118 B1 | 7/2001 | Alfano et al. | |
| 6,369,894 B1 | 4/2002 | Rasimas et al. | |
| 6,831,745 B2 | 12/2004 | Marquardt et al. | |
| 6,977,729 B2 | 12/2005 | Marquardt et al. | |
| 7,095,500 B2 | 8/2006 | Banks | |
| 7,154,603 B2 | 12/2006 | Banks | |
| 7,179,384 B2 | 2/2007 | Moriarty et al. | |
| 7,198,755 B2 | 4/2007 | Tokhtuev et al. | |
| 7,220,382 B2 | 5/2007 | Godfrey et al. | |
| 7,242,001 B1 | 7/2007 | Hedges et al. | |
| 7,550,746 B2 | 6/2009 | Tokhtuev et al. | |
| 2003/0141258 A1* | 7/2003 | Hatch | 210/745 |
| 2005/0229698 A1 | 10/2005 | Beecroft et al. | |
| 2006/0246595 A1 | 11/2006 | Banks et al. | |
| 2009/0150106 A1 | 6/2009 | Erickson | |
| 2009/0212236 A1 | 8/2009 | Tokhtuev et al. | |
| 2009/0283698 A1 | 11/2009 | Chapman | |

FOREIGN PATENT DOCUMENTS

JP     05072131 A     3/1993
(Continued)

OTHER PUBLICATIONS

English Abstract for JP 08313533 (A), published Nov. 29, 1996, Daikin Ind. Ltd., 1 page.
(Continued)

Primary Examiner — Cindy H Khuu
(74) Attorney, Agent, or Firm — Fredrikson & Byron, PA

(57) ABSTRACT

Some embodiments provide methods for calibrating a fluorometer in order to account for one or more optical properties of a water sample affecting fluorescence measurements. In some cases one or more calibration solutions are prepared with sample water from a specific field site. Fluorescence measurements are taken from a water sample and one or more of the calibration solutions, and calibration parameters are determined based on the measurements. In some cases a calibration solution is prepared by spiking sample water to include a higher concentration of a fluorescent tracer and measurements are taken to characterize a calibration slope coefficient. In some cases a calibration solution is prepared by adding an acid and measurements are taken to characterize a background fluorescence in the sample.

40 Claims, 16 Drawing Sheets

FOREIGN PATENT DOCUMENTS

| | | |
|---|---|---|
| JP | 08313533 A | 11/1996 |
| WO | WO2007064820 A3 | 6/2007 |
| WO | 2007143047 A1 | 12/2007 |

OTHER PUBLICATIONS

English Abstract for JP 05072131 (A), published Mar. 23, 1993, Kurita Water Ind. Ltd., 1 page.

International Search Report and Written Opinion, PCT/IB2011/051341, Aug. 29, 2011, 8 pages.

White, Audrey, Effect of pH on Fluorescence of Tyrosine, Tryptophan and Related Compounds, Dept. of Biochemisty, University of Sheffeld, Jul. 28, 1958, vol. 71, pp. 217-220.

Turner Designs, Aquafluor Handheld Fluorometer and Turbidimeter User's Manual, Sep. 2004, Version 1.3, pp. 1-36.

Turner BioSystems, Picofluor Handheld Fluorometer Operating Manual, Feb. 2010, Version 1.5, pp. 1-16.

\* cited by examiner

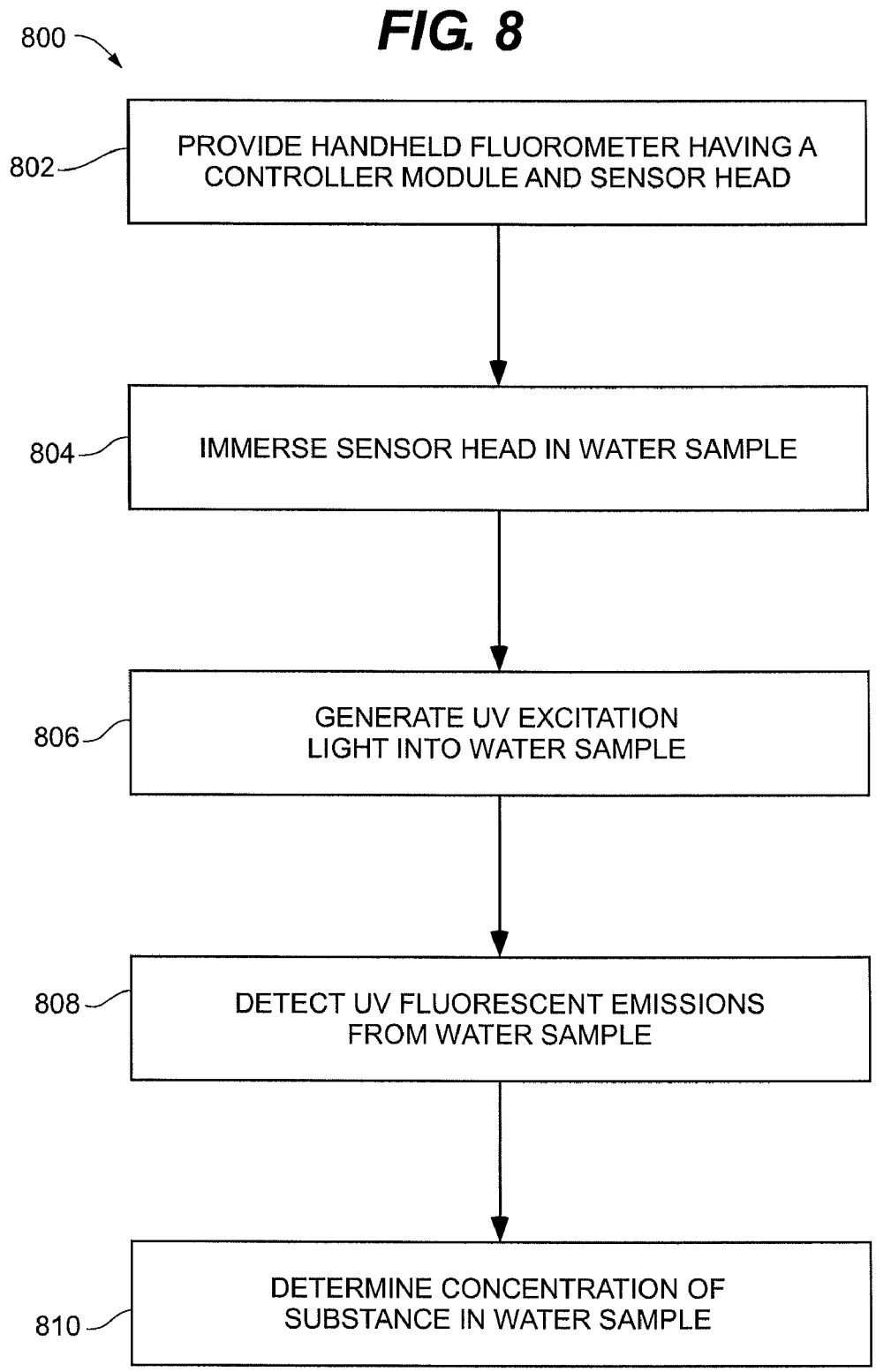

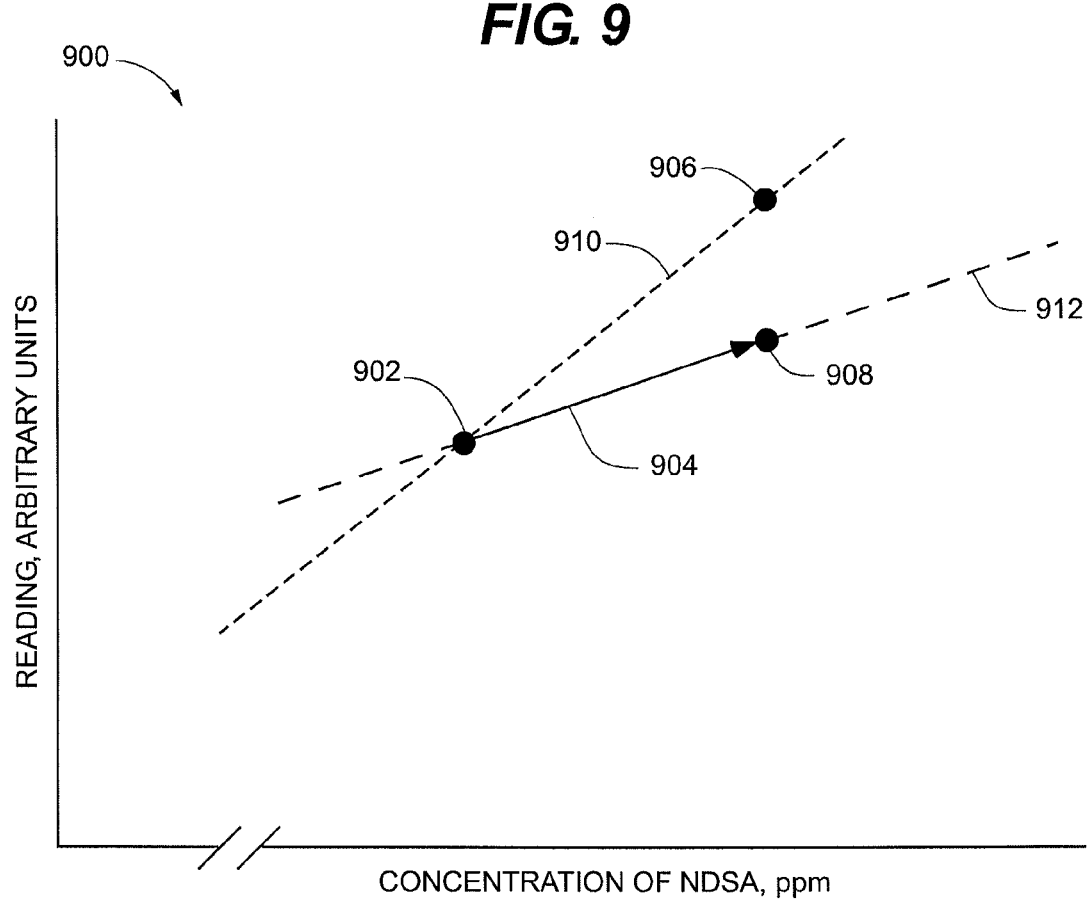

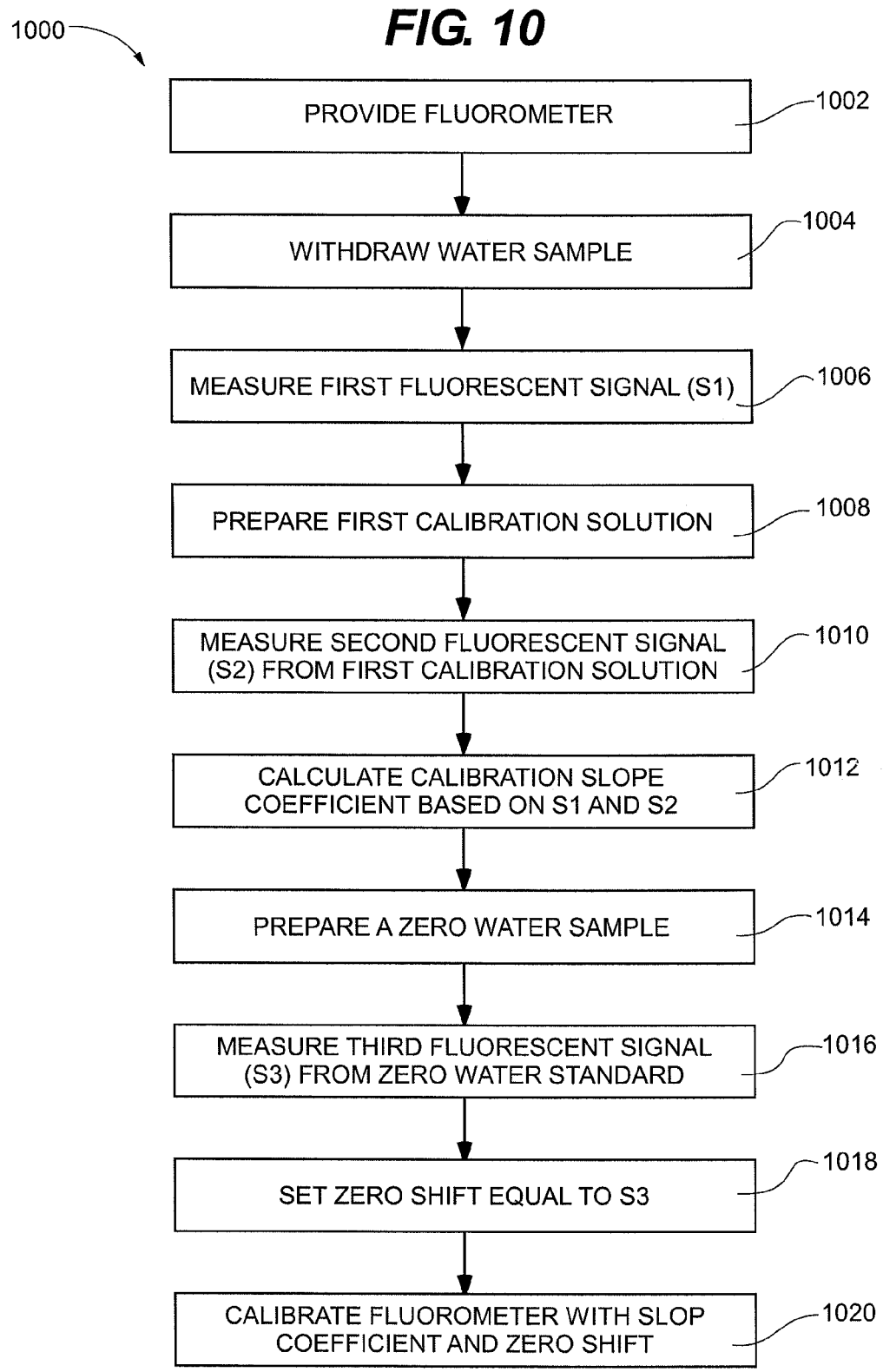

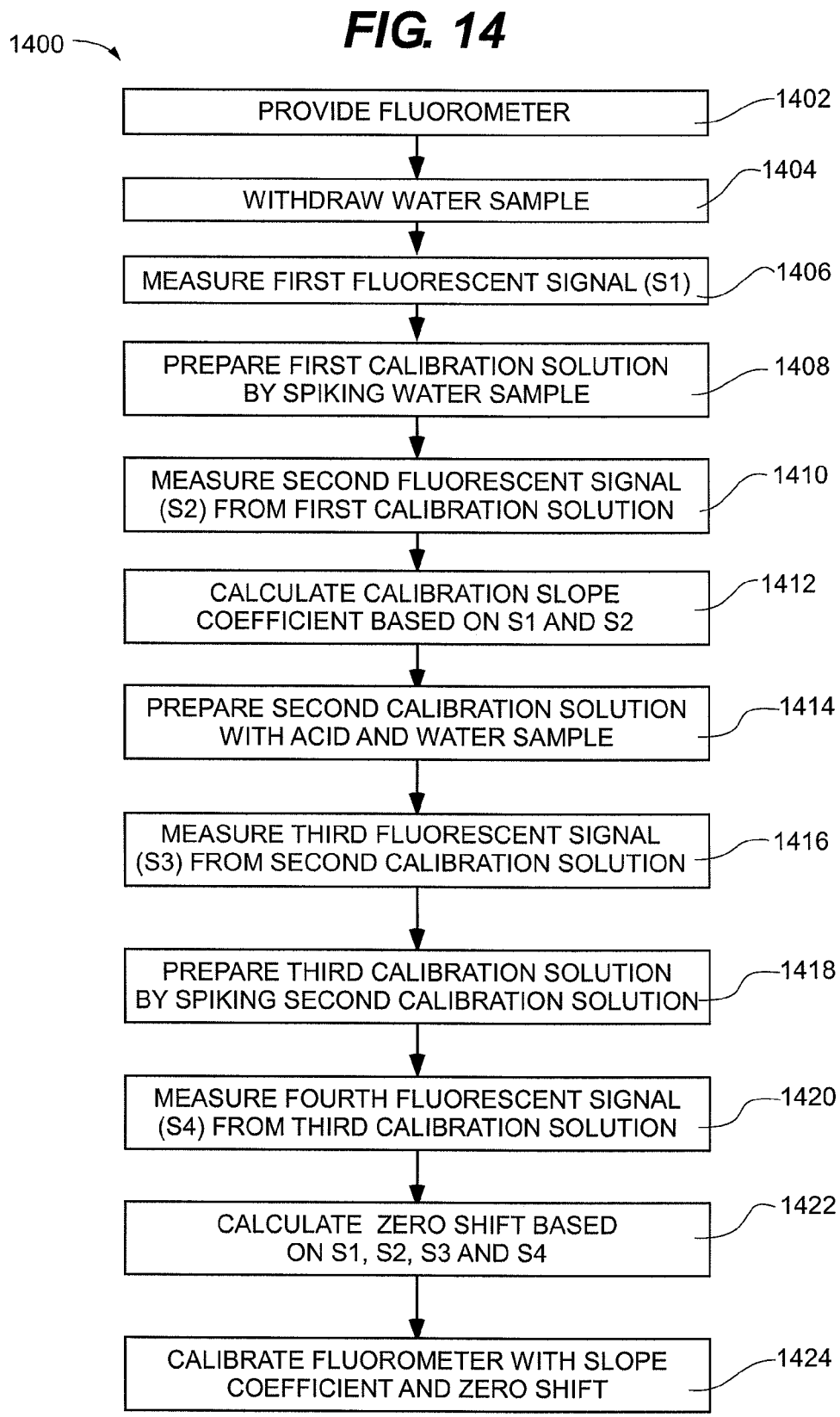

METHODS FOR CALIBRATING A FLUOROMETER

BACKGROUND

Embodiments of the present invention generally relate to fluorometric sensors and fluorometers for determining and monitoring the concentration of one or more substances in a liquid sample, and more particularly to the calibration of such fluorometric sensors and fluorometers.

In cleaning and antimicrobial operations, commercial users (e.g., restaurants, hotels, food and beverage plants, grocery stores, etc.) rely upon the concentration of the cleaning or antimicrobial product to make the product work effectively. Failure of a cleaning or antimicrobial product to work effectively (due to concentration issues) can cause a commercial user to perceive the product as lower quality. End consumers may also perceive the commercial user as providing inferior services. In addition, commercial users may be investigated and/or sanctioned by government regulatory and health agencies. Accordingly, there is a need for a system that can determine if the concentration of a product is within a specified concentration range. The same may be true for other applications, such as water care, pest control, beverage and bottling operations, packaging operations, and the like.

One method of monitoring the concentration of a product relies on monitoring the fluorescence of the product that occurs when the sample (and the product within the sample) is exposed to a predetermined wavelength of light. For example, compounds within the product or a fluorescent tracer added to the product may fluoresce when exposed to certain wavelengths of light. The concentration of the product can then be determined using a fluorometer that measures the fluorescence of the compounds and calculates the concentration of the chemical based on the measured fluorescence.

Fluorometric spectroscopy concerns the detection of fluorescent light emitted by a sample of interest. It involves using a beam of light, usually ultraviolet (UV) light, that excites the electrons in molecules of certain compounds in the sample and causes them to emit light of a lower energy (i.e., to "fluoresce"). There are several types of fluorometers for measuring emitted fluorescence. Fluorometers generally have of a source of excitation radiant energy, an excitation wavelength selector, a sample cell to contain the sample material, an emission wavelength selector, a detector with signal processor and a readout device. Filter fluorometers use optical filters to isolate the incident light and fluorescent light. Spectrofluorometers use diffraction grating monochromators to isolate the incident light and fluorescent light.

The accuracy of a fluorometer's measurements, and ultimately the accuracy of the calculated concentrations, depend upon the fluorometer's ability to account for various factors in the field. Accordingly, many fluorometers are calibrated prior to measuring fluorescence in order to correct for water properties such as background fluorescence that can significantly affect fluorescence measurements if not taken into account. In addition, water properties often vary over time and across sites, leading to further difficulty in obtaining accurate fluorescence measurements in the field.

SUMMARY

Some embodiments of the invention provide one or more methods for calibrating a fluorometer. In some cases one or more calibration methods take into account site-specific water properties and thus calibrate a fluorometer for a specific site in the field.

In some embodiments a method for calibrating a fluorometer includes providing a fluorometer that is configured to measure a fluorescent signal from a fluorescent marker in a sample of water from an industrial water system. The fluorometer is further configured to determine from the fluorescent signal a concentration of a water treatment product in the sample of water. A nominal concentration $C_0$ of the water treatment product corresponds to a nominal concentration $C_f$ of the fluorescent marker in the water sample. The method further includes withdrawing a water sample from the industrial water system and determining a slope coefficient, $K_m$, from the water sample and a zero shift, $Z_0$, from the water sample or a zero water solution.

According to one aspect of the invention, a calibration method further includes measuring a first fluorescent signal, $S_1$, from the water sample with the fluorometer and preparing a first calibration solution. The first calibration solution is prepared by preparing a spike solution containing the water treatment product at a concentration of about $P \times C_0$ and the fluorescent marker at a concentration of about $P \times C_f$, and adding about 1 part of the spike solution to about N parts of the water sample. A second fluorescent signal, $S_2$, is then measured from the first calibration solution with the fluorometer and the slope coefficient, $K_m$, is calculated as approximately equal to $$C_f \Big/ \left( S_2\left(\frac{N+1}{P}\right) - S_1\left(\frac{N}{N+1}\right) \right).$$

The method further includes measuring a third fluorescent signal, $S_3$, from a sample of the zero water solution and setting a zero shift, $Z_0$, equal to $S_3$. The fluorometer is then calibrated using the slope coefficient and the zero shift.

According to another aspect of the invention, a method for calibrating a fluorometer also includes measuring a first fluorescent signal, $S_1$, from the water sample with the fluorometer and preparing a first calibration solution. The first calibration solution is prepared by preparing a spike solution containing the water treatment product at a concentration of about $P \times C_0$ and the fluorescent marker at a concentration of about $P \times C_f$, and adding about 1 part of the spike solution to about N parts of the water sample. A second fluorescent signal, $S_2$, is then measured from the first calibration solution with the fluorometer and the slope coefficient, $K_m$, is calculated approximately equal to $$C_f \Big/ \left( S_2\left(\frac{N+1}{P}\right) - S_1\left(\frac{N}{N+1}\right) \right).$$

The method further includes preparing a second calibration solution to determine the zero shift. The second calibration solution is prepared by preparing an acid solution containing about Q % acid, and adding about 1 part of the acid solution to about M parts of the water sample. A third fluorescent signal, $S_3$, is then measured from the second calibration solution with the fluorometer. The zero shift, $Z_0$, is calculated as approximately equal to $$S_1 - S_3\left(\frac{M+1}{M}\right),$$

and the fluorometer is then calibrated using the slope coefficient and the zero shift.

According to another aspect of the invention, a method for calibrating a fluorometer includes measuring a first fluorescent signal, $S_1$, from the water sample with the fluorometer. A first calibration solution is prepared by preparing a spike solution containing the water treatment product in a concentration of approximately $100 \times C_0$ and the fluorescent marker in a concentration of about $100 \times C_f$, and adding about 1 part of the spike solution to about 99 parts of the water sample. A second fluorescent signal, $S_2$, is then measured from the first calibration solution with the fluorometer and the slope coefficient, $K_m$, is calculated as approximately equal to $C_f/(S_2-S_1\times 0.99)$. The method further includes preparing a second calibration solution to determine the zero shift. The second calibration solution is prepared by preparing an acid solution containing from about 5% to about 30% acid, and adding about 1 part of the acid solution to about 9 parts of the first calibration solution. A third fluorescent signal, $S_3$, is then measured from the second calibration solution and the zero shift, $Z_0$, is calculated as approximately equal to $S_2-(S_3\times 1.1)$. The method further includes calibrating the fluorometer with the slope coefficient and the zero shift.

According to another aspect of the invention, a method for calibrating a fluorometer includes measuring a first fluorescent signal, $S_1$, from the water sample with the fluorometer preparing a first calibration solution by preparing a first spike solution containing the water treatment product in a concentration of approximately $100 \times C_0$ and the fluorescent marker in a concentration of about $100 \times C_f$, and adding about 1 part of the first spike solution to about 99 parts of the water sample. A second fluorescent signal, $S_2$, is then measured from the first calibration solution with the fluorometer. The method also includes preparing a second calibration solution by preparing an acid solution containing from about 5% to about 30% acid, and adding about 1 part of the acid solution to about 9 parts of the water sample. A third fluorescent signal, $S_3$, is measured from the second calibration solution. The method also includes preparing a third calibration solution by preparing a second spike solution containing the water treatment product in concentration of approximately $100 \times C_0$ and the fluorescent marker in a concentration of about $100 \times C_f$ and adding about 1 part of the spike solution to about 99 parts of the second calibration solution. A fourth fluorescent signal, $S_4$, is measured from the third calibration solution with the fluorometer. In some cases the slope coefficient, $K_m$, is calculated as approximately equal to $C_f/(S_2-S_1\times 0.99)$. In some cases the zero shift, $Z_0$, is calculated as approximately equal to $$\left(S_1 - \frac{(S_2-S_1)(S_3-B_z(S_4-S_3))}{(S_4-S_3)}\right),$$

wherein $B_z$ is a background correction coefficient approximately between about 0.005 and about 0.05. The method further includes calibrating the fluorometer with the slope coefficient and the zero shift.

Some embodiments of the present invention can provide one or more of the following features and/or advantages. Some embodiments provide a calibration procedure that improves the accuracy of in-the-field fluorometer calibrations. Some embodiments take into account the on-site properties of the water system at a particular time to improve fluorometer calibration. Some embodiments account for one or more water properties such as background fluorescence, scattering, absorbance, turbidity, color, and other factors that can affect fluorescence measurements. In some cases, calibration methods provide an average accuracy of calibration of +/−2%. In some cases, the maximum calibration error is lower than 10%.

These and various other features and advantages will be apparent from a reading of the following detailed description.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 8 is a flow diagram depicting a method for determining a concentration of a substance in a water sample according to some embodiments of the invention.

FIG. 9 is a plot illustrating an effect of on-site water properties upon expected fluorescence measurements according to some embodiments of the invention.

FIG. 10 is a flow diagram illustrating a method of calibrating a fluorometer according to some embodiments of the invention.

FIG. 14 is a flow diagram illustrating a method of calibrating a fluorometer according to some embodiments of the invention.

DETAILED DESCRIPTION OF THE PREFERRED EMBODIMENTS

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments of the invention generally provide a number of methods for calibrating one or more types of fluorometers. In some embodiments a handheld fluorometer can advantageously be calibrated for on-site measurements of water treatment product concentrations at one or more different field locations. At each site, the fluorometer can be calibrated to correct for site-specific factors affecting fluorescence measurements at the particular time of measurement. While some embodiments herein are described with respect to calibrating a handheld fluorometer, it should be appreciated that embodiments of the invention are not limited to the calibration of any particular type of fluorometer and may be useful for calibrating a variety of fluorometer types.

Figure 1:
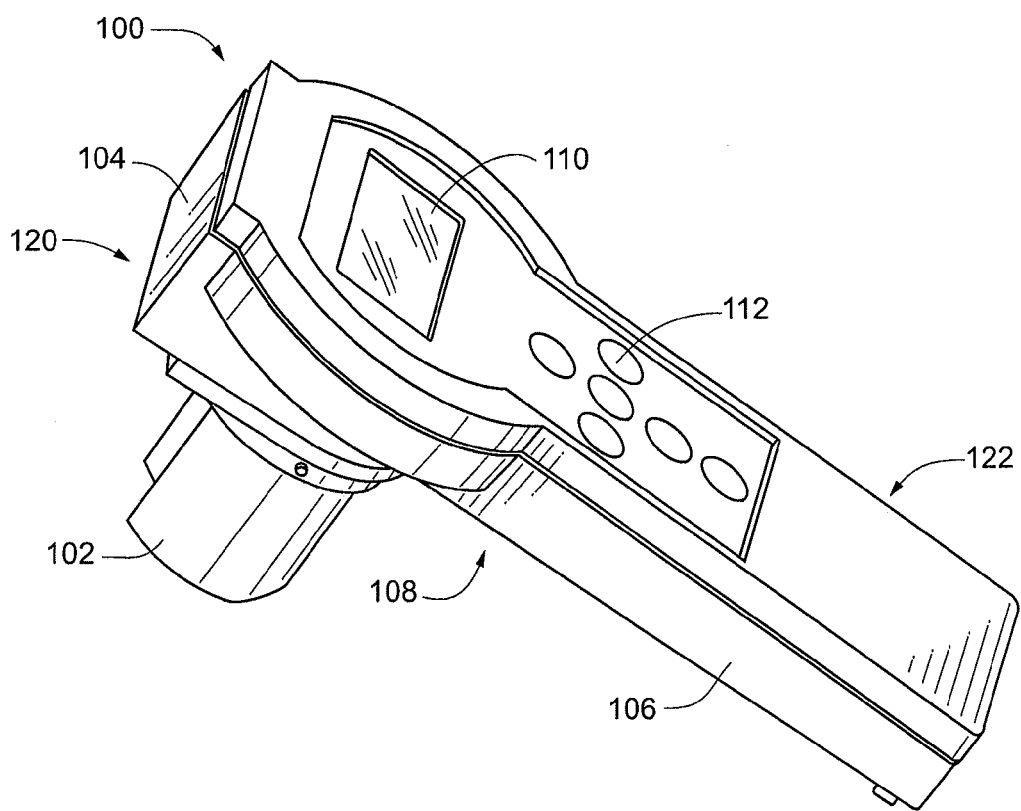
FIG. 1 is a perspective view of a handheld fluorometer according to some embodiments of the invention.

FIG. 1 is a perspective view of an optical measuring device in the form of a handheld fluorometer 100 that may be calibrated according to some embodiments of the invention. The fluorometer 100 generally includes an immersible sensor head 102 connected to a handheld controller module 104. The controller module 104 also includes an electronic display 110 for displaying sensor readings and calculations to a user, and an input interface in the form of a keypad 112 that allows the user to interact with the fluorometer 100 (e.g., entering variables, setting parameters, accessing menu items, etc.).

According to some embodiments, the controller module 104 has a generally elongated housing 106 which provides a convenient form, similar to a handle or wand, to easily grasp or hold the fluorometer 100 by the hand. The sensor head 102 preferably includes a water-tight housing that enables it to take measurements and otherwise function when partially or wholly immersed in a liquid sample of interest. Accordingly, in some cases the sensor head 102 has some features and/or characteristics similar to an immersible dip probe. For example, in some embodiments of the invention the immersible sensor head 102 has one or more features and/or components similar to those described in commonly-assigned U.S. Pat. No. 7,550,746 and U.S. Patent Application Publication 2009/0212236, the entire contents of each of which is hereby incorporated herein by reference. The configuration of the immersible sensor head 102 can also be contrasted in some ways with fluorometers and other optical instruments that position sensors and other components exterior to an optical cell containing the sample of interest.

In some cases the sensor head 102 is connected to (e.g., attached to or integral with) a bottom surface 108 of the controller housing 106 opposite from the display 110 and positioned proximate a distal end 120 of the controller housing. In a typical fashion, a user can grasp the controller housing 106 near a proximal end 122 of the controller housing to take measurements from a sample, read the display 110, and/or manipulate the keypad 112. For example, a user may dip the sensor head 102 into a sample by holding the controller module 104 above the surface of a liquid sample (e.g., in a reservoir/container in the field, a beaker in the laboratory, etc.) with the sensor head 102 partially or completely immersed in the sample. In some embodiments, a user may grasp the second end of the controller module 104 while securing a sample cup filled with a sample about the immersible sensor head 102. Of course other configurations of the controller module and the sensor head are possible and the invention is not limited to any particular physical configuration.

In general, the handheld fluorometer 100 at minimum measures fluorescent emissions from a sample including a substance of interest (e.g., a chemical solution, such as an antimicrobial or cleaning product), calculates a concentration of the substance in the sample, and displays the determined concentration to a user. The user can then optionally perform any desired actions based on the determined concentration, such as, for example, adding more of the substance to an industrial system in order to increase the concentration of the substance. In this way, the fluorometer can be part of a manual feedback loop. If the fluorometer determines that the concentration is lower or higher than a threshold concentration, a user will see the difference and can adjust the product dispensation appropriately by either dispensing more or less product. Additionally, the fluorometer can function as part of an out-of-product alarm. When a product runs out, the fluorescence (which reflects the concentration of the product) will drop below a pre-determined threshold level. At this point, the sensor can alert a user that the dispenser is out of product. The signal can be a visual or audio signal, or a vibrating signal. Accordingly, such feedback will ensure that enough cleaner, antimicrobial or other composition is present to achieve the desired effect (cleanliness, reduction in microorganisms, lubrication, etc.).

The basic operation of fluorometers is well known, and accordingly, various details are omitted here for conciseness and clarity. In general, the fluorometer 100 calculates a concentration of a particular substance in a liquid sample based on fluorescent properties of the substance. As will be described in more detail herein, the fluorometer 100 includes a light source that emits light within a selected wavelength range. When the sensor head 102 is immersed in the liquid sample, the light encounters particles of the substance of interest, which excites the electrons in certain molecules of the substance and causes them to emit light of a lower energy (i.e., to "fluoresce") in another wavelength range. The sensor head 102 includes an optical sensor, such as a photodetector, that detects the fluorescent emissions and generates a corresponding electrical signal indicating the intensity of the fluorescent emissions. The fluorometer 100 includes a controller, coupled with the optical sensor, that can then calculate the concentration of the substance based on a known relationship between the intensity of the fluorescent emissions and the concentration of the substance.

A number of variations and specific details of this general process are contemplated for embodiments of the invention involving fluorometers. For example, the substance of interest may be any desired chemical solution having fluorescent properties. Examples include, but are not limited to, biocides such as pesticide and antimicrobial products, anticorrosion, antiscaling, and antifouling products, disinfectants, and other cleaning products, detergents, additives, and the like. For convenience, these and other such substances are alternately referred to herein simply as "products," "chemical solutions," "treatment solutions" and the like. In addition, although examples are presented herein involving determining the concentration of water treatment product(s) or solution(s) within a sample of cooling water (e.g., a water sample) used in various industrial systems (e.g., a cooling tower), it should be appreciated that the handheld fluorometer 100 may be useful in determining the concentration(s) of products used in numerous settings to treat water and other liquids. As just a few examples, the handheld fluorometer 100 may be useful for determining concentrations of one or more substances in laundry, automatic ware-washing, manual ware-washing, 3$^{rd}$ sink applications, power sink applications, vehicle care, clean-in-place operations, healthcare applications, hard surface applications and the like.

Many products fluoresce in the presence of light radiating from the sensor head 102 because many of the compounds that make up the products have fluorescent characteristics. For example, a compound or molecule that has a benzene component can incorporate one or more substituent electron donating groups such as —OH, —NH$_2$, and —OCH$_3$, and polycyclic compounds that exhibit fluorescent characteristics. Many compounds used in the above-described applications include chemical structures like these, such as surfactants, lubricants, antimicrobial agents, solvents, hydrotropes, antiredeposition agents, dyes, corrosion inhibitors and bleaching additives. These compounds can be incorporated into products like ware-washing detergents, rinse aids, laundry detergents, clean-in-place cleaners, antimicrobials, floor coatings, meat, poultry and seafood carcass treatments, pesticides, vehicle care compositions, water care compositions, pool and spa compositions, aseptic packaging compositions, bottle washing compositions, and the like. Examples of some of these compounds and corresponding applications can be found in U.S. Pat. No. 7,550,746, the entire content of which is herein incorporated by reference.

Additionally, or alternatively, fluorescent tracers (also referred to herein as "fluorescent markers") can be incorporated into products that may or may not already include naturally fluorescing compounds. Some non-limiting examples of tracers include naphthalene disulfonate (NDSA), 2-naphthalenesulfonic acid, Acid Yellow 7,1,3,6,8-pyrenetetrasulfonic acid sodium salt, and fluorescein. In some embodiments the fluorescent tracer is added to the product in a known proportion, thus making it possible to estimate the concentration of the product once the concentration of the tracer is determined. For example, in some cases the concentration of the fluorescent tracer can be determined by comparing a current fluorescent signal with fluorescent signals from known tracer concentrations measured during a calibration procedure. The concentration of chemical product can then be estimated from the known nominal proportion of fluorescent tracer and measured concentration of fluorescent tracer. In some cases a current concentration of a product, $C_c$, in a liquid sample can be determined by $$C_c = C_m \times (C_0/C_f), \text{ wherein}$$

$$C_m = K_m \times (S_x - Z_0), \text{ and}$$

wherein $C_m$ is a current fluorescent marker concentration, $K_m$ is a slope correction coefficient, $S_x$ is a current fluorescent measurement, $Z_0$ is a zero shift, $C_0$ is a nominal concentration of the product, and $C_f$ is a nominal concentration of the fluorescent tracer.

Figure 2:
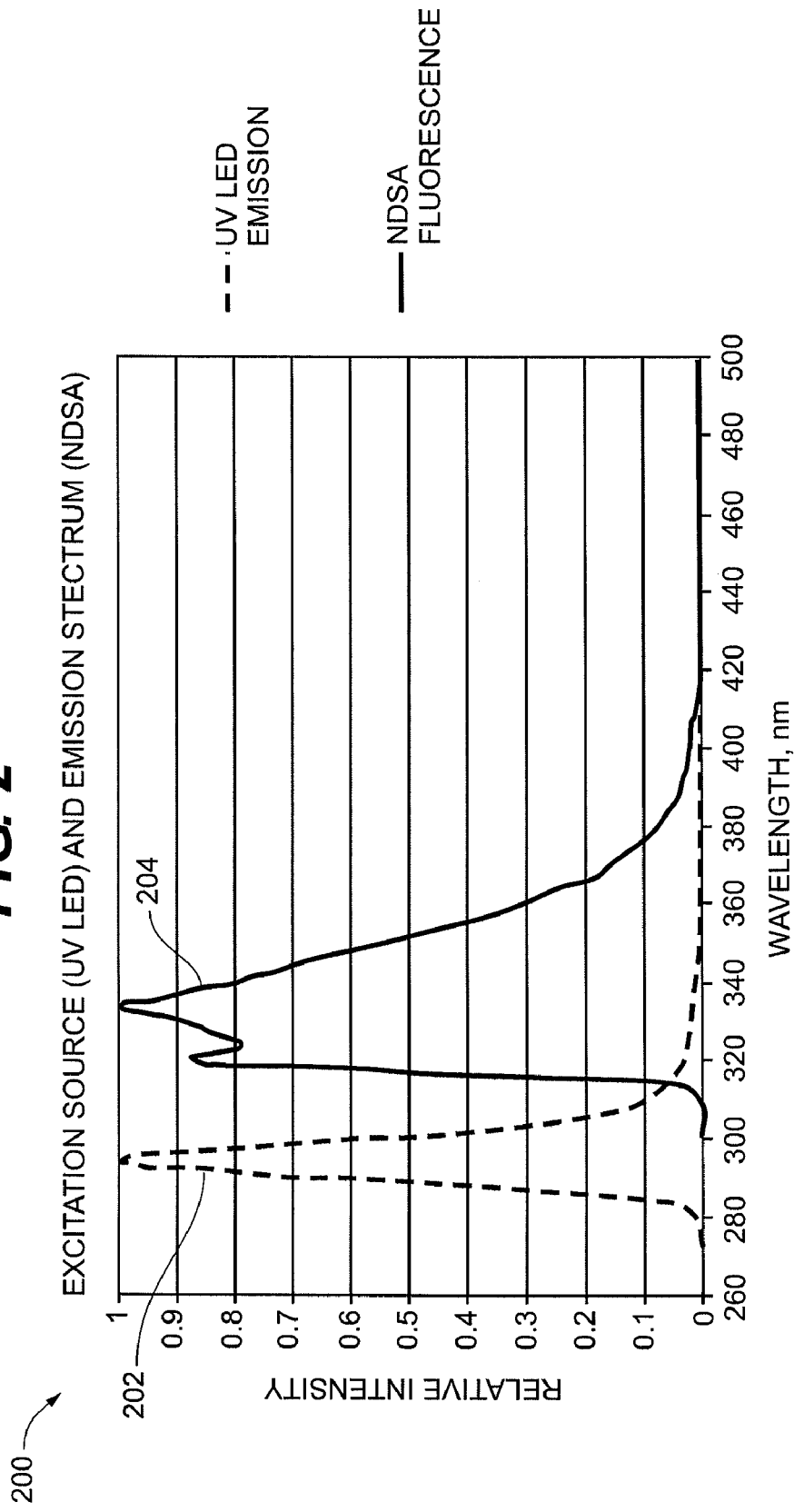
FIG. 2 is a plot of excitation and emission spectrum intensity according to some embodiments of the invention.

Referring to FIG. 2, a plot 200 is shown of an excitation spectrum intensity 202 and an emission spectrum intensity 204 according to some embodiments of the invention. In this example, a fluorometer having a light source in the form of an ultra violet (UV) light emitting diode (LED) emits excitation light within a range from about 280 nm to about 310 nm into a sample of cooling tower water having a product with an added fluorescent tracer, NDSA. The added NDSA absorbs this UV radiation and produces fluorescence in a range from about 310 nm to about 400 nm. The emission detector of the fluorometer detects this emitted radiation, and the fluorometer determines the concentration of the NDSA tracer, and ultimately the concentration of the product within the sample of the cooling tower water.

Figure 3:
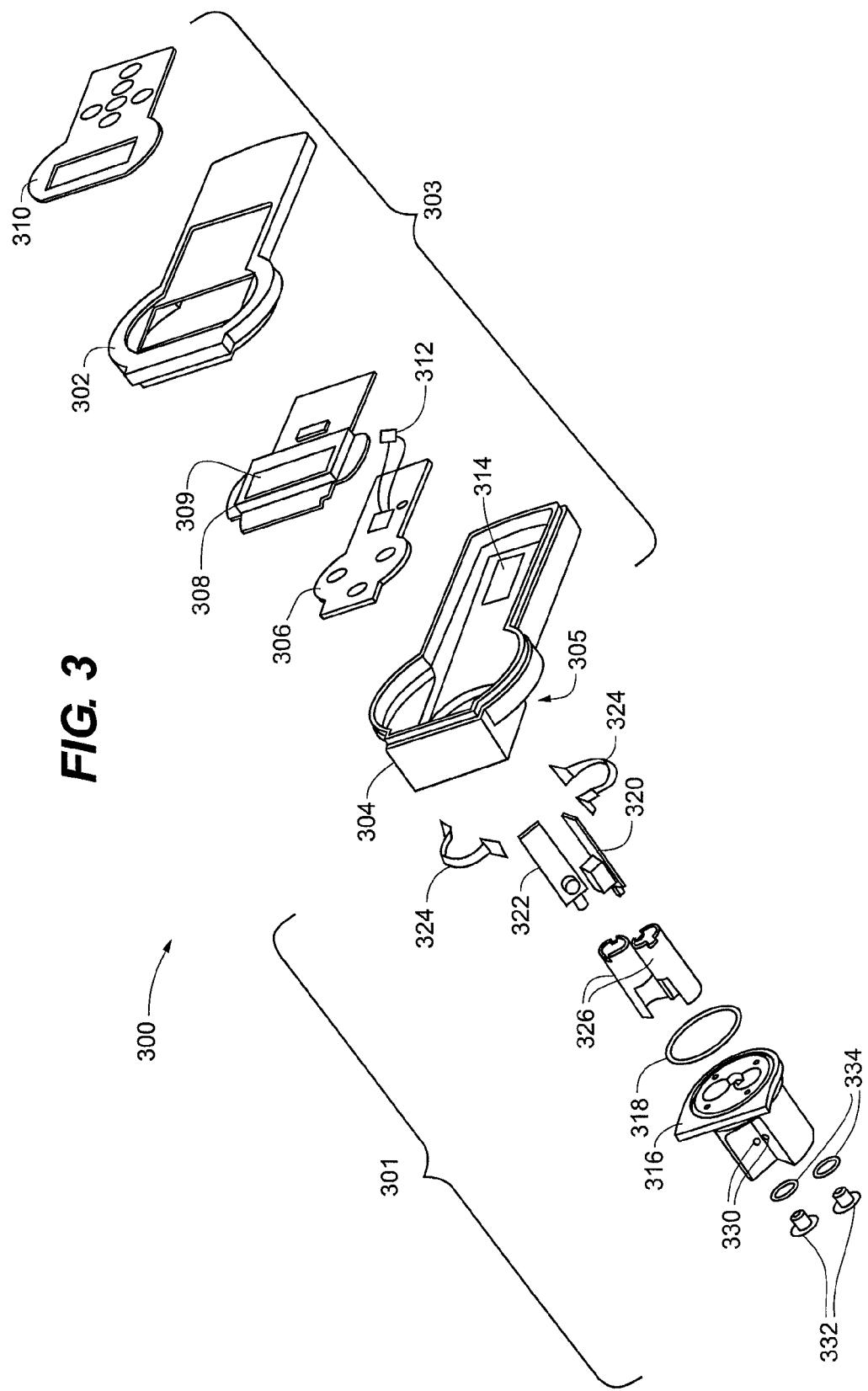
FIG. 3 is an exploded view of a handheld fluorometer according to some embodiments of the invention.

FIG. 3 is an exploded view of a handheld fluorometer 300 similar to the handheld fluorometer shown in FIG. 1. The fluorometer 300 generally includes an immersible sensor head 301 connected to a controller module portion 303. The controller module 303 includes a housing and several components within the housing. The housing is formed from a top portion 302 and a bottom portion 304, with the bottom portion 304 of the controller housing defining a bottom surface 305 on the exterior of the bottom portion. The sensor head 301 includes a sensor head housing 316 that is configured to be fixedly attached to the bottom surface 305 of the controller housing. In some embodiments the sensor head housing 316 may be integrally formed with one or more portions of the controller housing.

In some embodiments the controller module 303 generally includes those components necessary to determine a concentration of a product based on a signal received from the sensor head 301. As shown in FIG. 3, the controller module 303 includes a control board 306 that couples with a display board 308 via a display board cable 312. The display board 308 includes an electronic display 309 (e.g., an LCD screen) that displays information to a user. The controller module 303 also includes an input interface in the form of a membrane keypad overlay 310, which allows the user to enter a variety of information for use by the controller module 303. The controller module 303 also includes a portable power source, e.g., battery, 314 for powering the circuits within the fluorometer 300.

In some embodiments the immersible sensor head 301 has one or more features and/or components similar to those described in commonly-assigned U.S. Pat. No. 7,550,746 and U.S. Patent Application Publication 2009/0212236, the entire contents of each of which is hereby incorporated herein by reference. Referring back to FIG. 3, in some embodiments, the sensor head 301 includes a housing 316 that houses a light source board 320 and an emission detector board 322. A first O-ring 318 provides a seal between the sensor head housing 316 and the bottom portion 304 of the controller housing. The components on the light source board 320 and the emission detector board 322 are shielded by a brass tube 326 that substantially encircle each board. Each tube 326 includes a cutout at the distal end of the tube, and the sensor head housing 316 includes windows 330 extending through the housing. These cutouts and the windows 330 allow a light source (e.g., LED) positioned on the light source board 320 and an emission detector (e.g., photodetector) positioned on the emission detector board 322 to communication with an analytical area outside the sensor head housing 316. Electrical cables 324 couple the light source board 320 and the emission detector board 322 to the control board 306, which allows the controller on the board 306 to control the light source and receive signals back from the emission detector. In some embodiments the sensor head 301 also includes one or more temperature sensors that are able to measure the temperature of a water sample. For example, the light source board 320 and/or the emission detector board 322 may include one or more temperature sensors that extend into the sensor head housing 316. Covers 332 positioned in a distal face of the sensor housing 316, along with additional O-rings 334, provide a seal around the temperature sensors.

Figure 4:
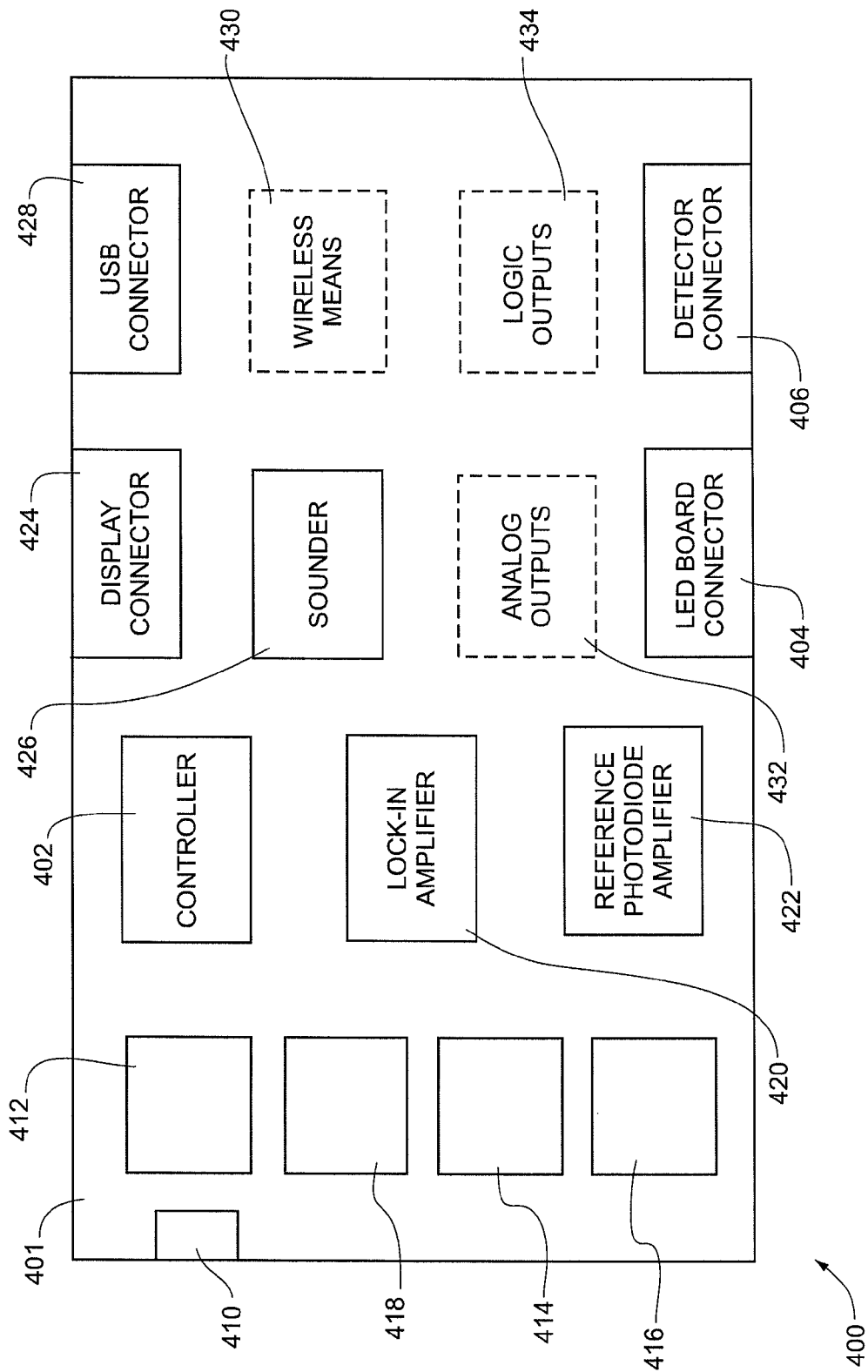
FIG. 4 is a schematic diagram of a controller board according to some embodiments of the invention.

FIG. 4 is a schematic diagram of a controller board 400 for a handheld fluorometer according to some embodiments of the invention. The controller board 400 can comprise a number of discrete components positioned (e.g., soldered) and coupled together (connections not shown) on a printed circuit board 401. FIG. 4 presents a simplified schematic of the basic components of one exemplary control board 400, and it will be appreciated by those skilled in the art that various connections between the components and/or details about components may vary. The control board 400 includes a controller 402, which calculates a concentration of a product within a water sample based on an intensity signal from the emission detector. The controller 402 may provide a variety of other functions, including without limitation, performing a calibration routine, accepting and executing instructions entered at the input interface, and/or formatting data for viewing on the fluorometer's display. The controller 402 can be embodied in any suitable form, such as a software driven microprocessor, a microcontroller, or a field programmable gate array, or a fixed hardware design such as an application specific integrated circuit, etc. In addition, the controller 402 may have onboard memory, or the control board may have memory (not shown) that stores instructions for execution by the controller 402.

The control board also includes a power cable with a connector 410 for connecting the board 400 to a power source such as the battery 314 shown in FIG. 3. The board 400 also includes a controller power supply 412, an analog power supply 414, and a light source power supply 416 for powering the light source in the sensor head. In some embodiments the control board 400 includes a real-time clock battery 418, a lock-in amplifier 420, a reference photodiode amplifier 422, and connectors for the display board 424, the light source board 404, and the emission detector board 406. In some cases, the control board 400 may also have a sounder 426, a USB or other type of data connector 428, wireless means 430 for communicating with other computing devices, and optional analog 432 and logical 434 outputs.

Figure 5:
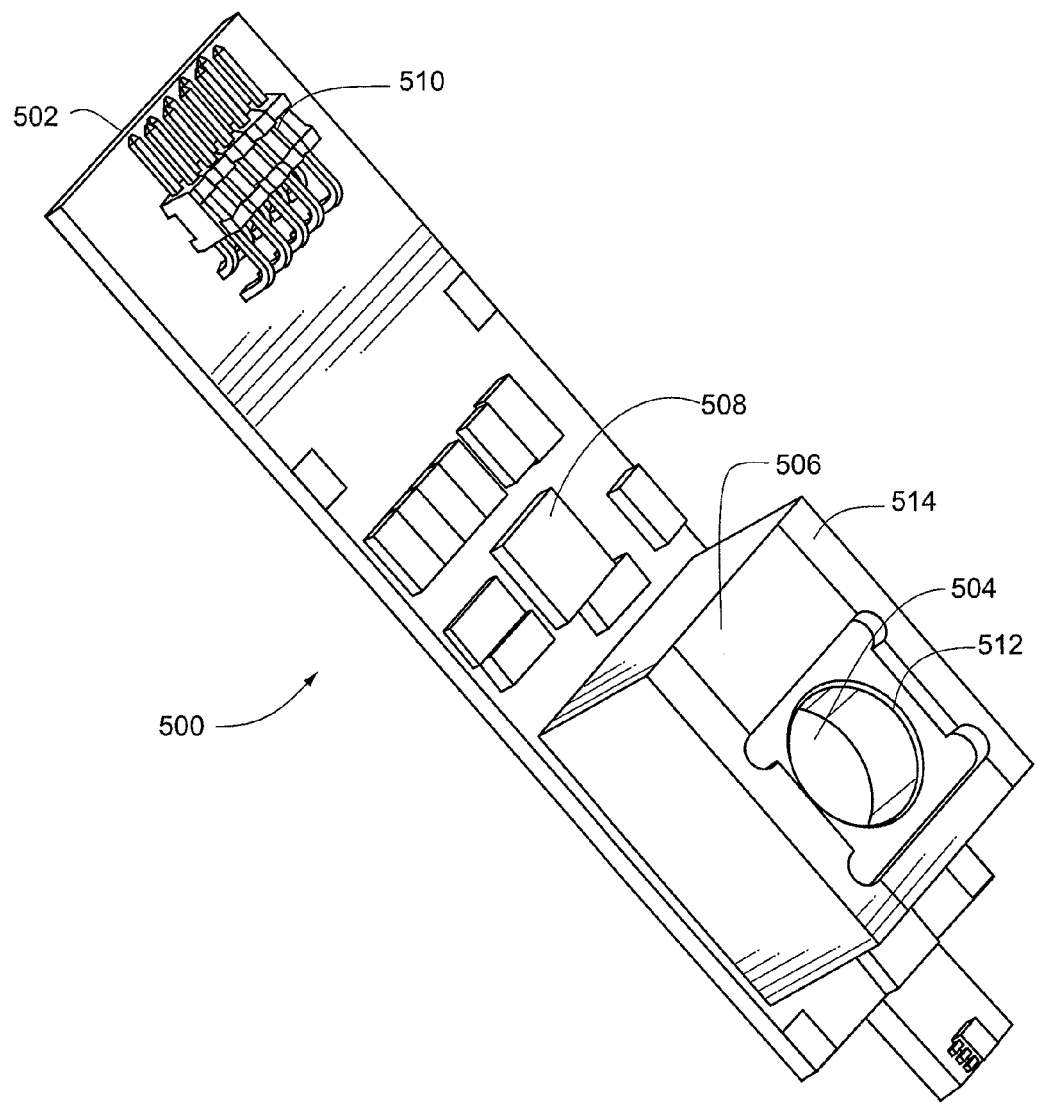
FIG. 5 is a perspective view of a light source board according to some embodiments of the invention.

FIG. 5 is a perspective view of a light source board 500 according to some embodiments of the invention. The board 500 (also shown in FIG. 3 as 320) generally includes a printed circuit board 502 having a light source 504 and a reference photodiode 506, along with a preamplifier 508 and a connector 510 for coupling the board 500 with the control board. An excitation filter 512 is positioned by a filter holder 514 over the light source 504, to filter the light from the light source 504 before it leaves the immersible sensor head. The light source 504 can include a variety of possible elements. For example, light source 504 may be a gas discharge lamp, a mercury lamp, a deuterium lamp, a metal vapor lamp, a light emitting diode (LED) or a plurality of LEDS. In addition, the light source 504 may emit excitation radiation in a number of possible spectrums depending upon the element chosen and the spectrum desired. In some embodiments the light source is an ultraviolet LED, capable of emitting light having a wavelength from about 280 nm to about 310 nm.

Figure 6:
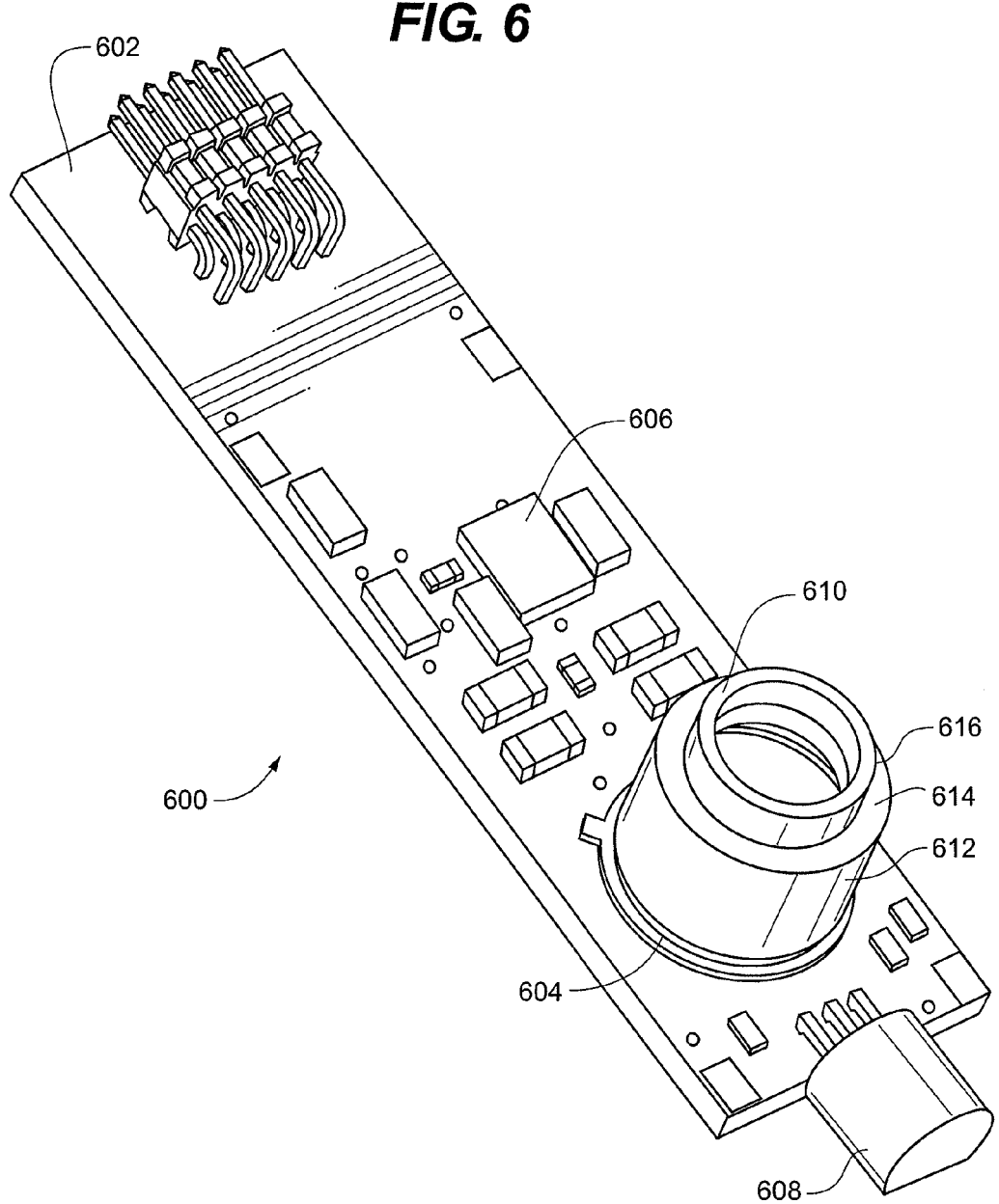
FIG. 6 is a perspective view of an emission detector board according to some embodiments of the invention.

FIG. 6 is a perspective view of an emission detector board 600 according to some embodiments of the invention. The detector board 600 generally includes a number of components, including an emission detector 604 positioned on a printed circuit board 602. In some embodiments of the invention, the emission detector 604 comprises a UV-sensitive photodiode. For example, the detector 604 may generate an intensity signal based on light from about 310 nm to about 400 nm that it detects from an analytical area outside the sensor head. The detector board 600 also includes a preamplifier 606 and a temperature sensor 608. An emission filter holder 610 positioned about the emission detector 604 supports one or more filters for screening the radiant energy and passing on the desired wavelengths to the detector 604. In the embodiment shown in FIG. 6, the filters include an interference filter 612 and a UG-11 glass filter 614. In some embodiments, an additional polyester film filter 616 is also positioned in front of the emission detector 604. In some cases the polyester film filter 616 has a thickness of about 0.5+/−0.2 mm. In some cases optical designs can provide increased optical efficiency (e.g., using ball lenses, highly divergent beams, etc.) but may also compromise the performance of interference filters which have a high efficiency and a high rejection value for collimated beams. Incorporating such a polyester film can in some cases minimize stray light levels to allow measurements of NDSA fluorescence in samples with a turbidity as high as 100 Nephelometric Turbidity Units (NTU).

Figure 7A:
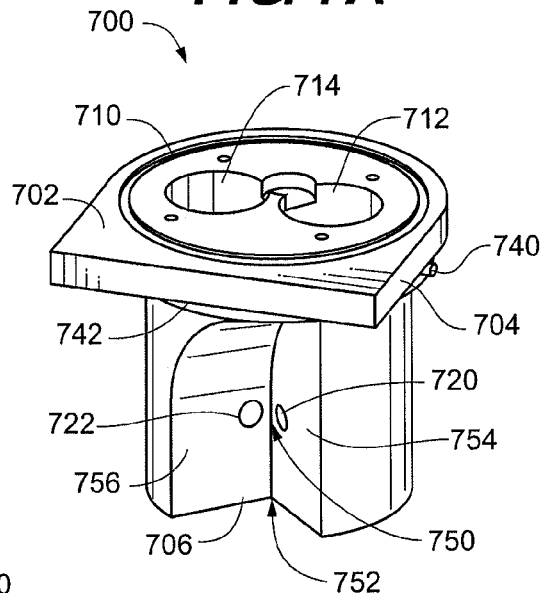
FIG. 7A is a top perspective view of a sensor head according to some embodiments of the invention.
Figure 7B:
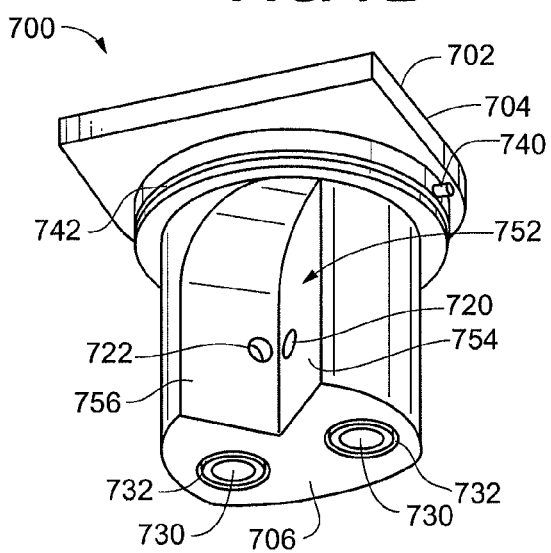
FIG. 7B is a bottom perspective view of the sensor head of FIG. 7A.
Figure 7C:
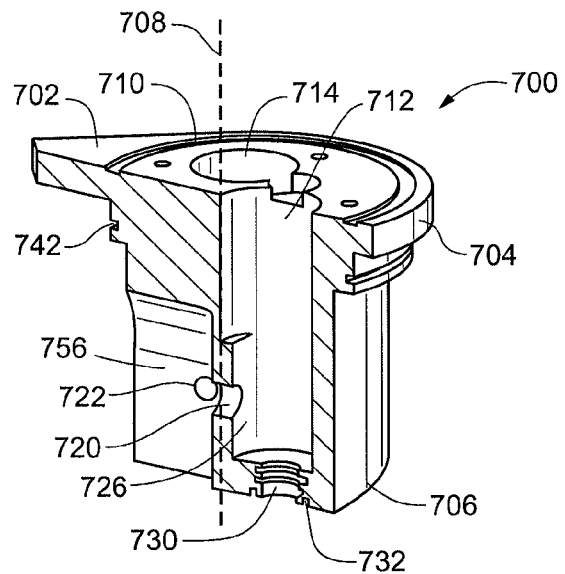
FIG. 7C is a perspective, cross-sectional view of the sensor head of FIG. 7A.

FIGS. 7A-7C present various views of a discrete immersible sensor head 700 according to some embodiments of the invention that can be attached to a controller module of a handheld fluorometer such as of those previously discussed. FIG. 7A is a top perspective view of the sensor head 700, FIG. 7B is a bottom perspective view of the sensor head 700, and FIG. 7C is a perspective, cross-sectional view of the sensor head 700. The sensor head 700 can be made from a plastic and may be molded and/or milled to achieve the desired shape and features.

In general, the sensor head 700 comprises a housing 702 that includes a first vertical cavity or chamber 712 that is configured to receive a light source circuit board (e.g., the light source board 320 of FIG. 3 or 500 of FIG. 5). In some cases the light source chamber 712 is formed with a cylindrical configuration, which can provide a snug fit for the cylindrical brass shields 326 illustrated in FIG. 3. In some embodiments the light source chamber 712 has a partially-cylindrical configuration including a planar wall 726 along one lateral side of the chamber 712. Returning to FIGS. 7A-7C, the sensor head housing 702 includes a second vertical cavity or chamber 714 for receiving an emission detector circuit board (e.g., the emission detector board 322 of FIG. 3 or 600 of FIG. 6), similar to the light source chamber 712. In some cases the light source chamber 712 and the emission detector chamber 714 may be formed and positioned symmetrically about a longitudinal axis 708 of the sensor head 700, although this is not required in all embodiments.

The sensor head housing 702 further includes an angular cutout 752 in the exterior surface of the housing 702. In some embodiments the angle of the cutout 752 is approximately 90 degrees, although it should be understood that the invention is not limited to a particular angle for the cutout. The cutout 752 is bounded by a first wall 754 intersecting a second wall 756 at the longitudinal axis of the sensor head 700. The first wall 754 defines a light source window 720 that provides a path through the first wall 754 for excitation energy emitted by the light source. The second wall 756 similarly defines a emission detector window 722 that provides a path through the second wall 756 for fluorescent emissions to reach the emission detector located within the sensor head housing 702. In some embodiments, the light source window 720 and/or the emission detector window 722 comprise a channel extending through the sensor head housing 702. In some embodiments the windows 720, 722 also include a lens, prism or other material optically transparent to the light source radiation and/or fluorescent emissions. For example, in some embodiments a glass or sapphire ball lens is positioned within each channel. Other suitable materials known in the art may also be used. The ball lens provides the light source/detector window, but also provides a focusing means for directing light between the light source/detector and an analytical area 750 outside the housing 702 of the sensor head 700.

As shown in the figures herein, the angular cutout 752, including the light source window 720 and the emission detector window 722, are oriented with respect to the controller module such that the angular cutout and the windows face toward the distal end of the controller module. As discussed further herein, the angular cutout and the windows may be oriented in a different direction in some embodiments. For example, in some embodiments the angular cutout and the windows face toward the proximal end of the controller module.

In some embodiments, the sensor head 700 includes a proximal end 704 and a distal end 706, between which extends the longitudinal axis 708 and a length of the sensor head 700. As shown in FIGS. 1 and 3, in some embodiments the sensor head 700 is connected to the bottom surface of the controller module housing at or near the proximal end 704 of the sensor head 700. In some cases the sensor head 700 may be fixedly attached to the controller housing with a fastener. The fastener can include, but is not limited to, screws, bolts, and/or pins, or an adhesive or weld (not shown in the figures). In some embodiments the sensor head 700 is secured with four screws that compress an O-ring positioned in a groove 710 between the sensor head 700 and the controller module. In some embodiments, the sensor head housing 702 may be integrally formed with the controller module such that there is a seamless transition between the proximal end 704 of the sensor head and the bottom surface of the controller module.

In some embodiments the sensor head 700 also includes part or all of a fastener that removably fastens a sample cup about the sensor head 700. As just one example, the fastener may comprise one or more pins 740 positioned about the sensor head housing 702 and corresponding slots on the sample cup. In some embodiments the pins 740 and the slots form a bayonet fastener that secures the sample cup about the sensor head and also aligns the sample cup in a preferred orientation (e.g., rotation) about the sensor head 700. Other fasteners (e.g., screw threads, opposing pressure elements, etc.) can also be included.

In some embodiments the sensor head 700 also includes holes 730 for inserting one or more temperature sensor covers, such as those depicted in FIG. 3. Returning to FIGS. 7A-7C, the holes 730 may be threaded or otherwise configured to receive and secure the temperature sensor covers. The temperature sensors (not shown in FIGS. 7A-7C) are adapted to sense the current temperature of the water sample and generate a corresponding signal that can be used to correct concentration calculations based on errors due to, e.g., temperatures outside an acceptable range.

In addition, the sensor head 700 is preferably an immersible sensor head, meaning that it is partly or wholly immersed below the surface of a water sample when taking fluorescent emission measurements. Accordingly, the sensor head housing 702, connection to the controller housing, and any windows or other potential voids in the housing 702 are effectively sealed prior to immersion. For example, in some cases the housing 702 includes a first O-ring groove 710 at the proximal end 704 of the sensor head and second O-ring grooves 732 around the temperature sensor holes 730. In some embodiments including a sample cup, a third O-ring groove 742 may also be formed around the circumference of the sensor head 700 near the proximal end 704 of the sensor head in order to provide a substantially impermeable seal between the sample cup and the sensor head 700. In addition, the light source window 720 and emission detector window 722 may also be sealed with O-rings and the like. In some embodiments, the light source window 720 and emission detector window 722 are sealed due to a pressure fit between the window channels and the ball lenses placed within the channels.

FIG. 8 is a flow diagram depicting a method of determining a concentration of a product in a water sample according to some embodiments of the invention. In general, the fluorometer measures a fluorescent light emission of the active molecule in the product that is proportional to the actual concentration of the product in the water sample. After providing a handheld fluorometer having a controller module and a sensor head connected to the controller module (802), a water sample containing the product of interest is provided. The sensor head is immersed in the water sample (804) and the water sample occupies an analytical area of the sensor. Next, an ultraviolet (UV) excitation light having a first UV wavelength is generated by a light source in the sensor head and directed into the water sample and the analytical area (806). The sensor head then detects and measures the fluorescent emissions of the sample at a second UV wavelength (808). The sensor head includes a controller (402 in FIG. 4, for example) that calculates the concentration of the product in the sample based on the measured fluorescent emissions (810). The first wavelength may be in the range of 280-310 nm. The second UV wavelength may be in the range of 310 nm to 400 nm. The sensor may also measure a reference fluorescence emission of the sample at the first wavelength. The sensor may also measure a fluorescence emission of a zero solution having zero concentration of the chemical. In that case, the concentration of the chemical in the sample may be calculated based on the calculated difference in the measured fluorescence emission of the sample containing the chemical and the measured fluorescence emission of the zero solution. The concentration of the sample may also be calculated based on a calibration constant determined for known concentrations of the product in a calibration sample.

As an example, in some cases sample concentrations may be evaluated based upon signals from two UV detectors. A reference detector measures an intensity of the UV excitation generated by the light source, while a fluorescent emission detector measures an intensity of the fluorescent emissions emitted by the product. The calculation uses the following equations:

$$C_C = K_X \left( \frac{I_E^S}{I_R^S} - \frac{I_E^0}{I_R^0} \right)$$

where $C_C$ is an actual, current concentration of a product X (for example, a surfactant, an antimicrobial agent, etc) in a sample solution;

$K_X$ is a calibration coefficient;

$I_E^S$ is an output signal from the emission detector for the sample solution;

$I_R^S$ is an output signal from the reference detector for the sample solution;

$I_E^0$ is an output signal from the emission detector for a zero solution (i.e., a solution with zero concentration of the product); and $I_R^0$ is an output signal from the reference detector for the zero solution.

$$K_X = C_{CALIBR} \bigg/ \left( \frac{I_E^{CALIBR}}{I_R^{CALIBR}} - \frac{I_E^0}{I_R^0} \right)$$

where $C_{CALIBR}$ is a concentration of the product in a calibration solution;

$I_E^{CALIBR}$ is an output signal from the emission detector for the calibration solution; and $I_R^{CALIBR}$ is an output signal from the reference detector for the calibration solution.

As discussed above with reference to FIG. 4, the controller 402 within the handheld fluorometer can calculate the concentration of the product in a sample based on the intensity signal from the emission detector. In some embodiments the controller 402 may also calculate the product concentration based on a calibration constant, zero shift, and/or an excitation reference signal using the relationships described above. Operation instructions for the controller may be stored in an onboard or discrete memory. In that respect, the memory may be a computer-readable medium comprising program instructions that cause the controller to provide any of the functionality ascribed to them, and perform any of the methods described herein. The controller may also store the raw fluorescence data obtained by the emission and/or reference detector(s) and other pertinent data in the memory. The controller may also store any calculated fluorescence values and/or concentration data in the memory.

As discussed above herein, in some embodiments of the invention a fluorometer can measure a fluorescent emission from a water sample and provide a calibrated calculation of a product concentration that accounts for one or more properties of the sample water that can affect the fluorescence measurement. FIG. 9 is a plot 900 illustrating some effects of on-site water properties upon expected fluorescence measurements according to some embodiments of the invention. The plot 900 generally charts possible fluorometer readings in arbitrary units (e.g., in terms of fluorescence, concentration, etc.) versus a concentration of a fluorescent tracer, NDSA, in the water sample. An initial measurement 902 provides a reference point for successive measurements. In some embodiments the water sample has a volume that is at least two or more times greater than a minimum volume needed to take a fluorometric reading with the fluorometer.

In some cases, the initial measurement 902 provides limited information about the actual concentration of fluorescent tracer (as shown with the broken concentration axis in FIG. 9) and additional calibration is necessary to further characterize the relationship between product tracer concentration and fluorometer readings. A calibrated calculation may be based in part on one or more calibration factors, such as a calibration constant (e.g., calibration slope coefficient), a zero shift, and/or an excitation reference signal. For example, in some cases the current fluorescent marker concentration, $C_m$ is approximately equal to $K_m \times (S_x - Z_0)$, wherein $S_x$ is a current fluorescent measurement, $K_m$ is a calibration slope correction coefficient, and $Z_0$ is a zero shift. In some cases a current concentration of a product, $C_c$, can then be determined as approximately equal to $C_m \times (C_0/C_f)$, wherein $C_0$ is a nominal concentration of the product, and $C_f$ is a nominal concentration of the fluorescent tracer. In some embodiments of the invention, a nominal concentration of NDSA is from about 0.1 ppm to about 3 ppm. In some embodiments, the nominal concentration of NDSA is about 0.5 ppm.

In some cases, a calibrated relationship between the concentration of the fluorescent marker (and product) with respect to the fluorometer reading can be described in terms of a zero shift and a calibration slope. Use of the zero shift corrects a reading for effects caused by background fluorescence, basically subtracting out the measured background fluorescence so that the reading only corresponds to fluorescence emitted by the tracer/product. The calibration slope provides an indication of the expected increase in fluorometer reading that can be expected for a given increase in concentration of the tracer within the sample.

Returning to FIG. 9, when the concentration of NDSA is increased from the initial measurement 902, shown by arrow 904, it may be expected that a next measurement 906 would correspond to a reading along an expected curve 910 that is based on known increases in fluorescence readings for known increases in tracer concentration. For example, increases in fluorescence readings are often determined for increments in concentration by measuring the fluorescence of a zero sample after increasing a tracer concentration in the zero sample by a known amount. Referring to FIG. 9, however, the inventors have surprisingly discovered that after increasing the concentration of tracer in a field sample by a known amount, a next measurement 908 yields a different reading along a different curve 912 than may be expected during calibration with a zero sample. Without being bound by a particular theory, the inventors believe the difference is caused by effects on the tracer fluorescence caused by absorbance, scattering, color, turbidity, and the like in the actual water sample. Some embodiments of the invention provide methods for calibrating a fluorometer that take into account the effect of actual water sample optical properties on the fluorescence of the tracer in addition to background fluorescence effects. In this way, the actual calibration curve 912 can be determined with an actual slope and a zero offset corresponding to the curve's intersection with the reading axis, being offset from the concentration axis.

In some embodiments, the slope of the actual calibration curve 912 can be determined by forming a calibration solution with a water sample from the industrial water system being tested and a known amount of fluorescent tracer added to the sample. Referring to FIG. 10, in some embodiments a method 1000 for calibrating a fluorometer includes steps for determining the calibration slope and the calibration offset. The method 1000 includes providing a fluorometer (1002), such as one of those described above herein or another, withdrawing a water sample (1004), and measuring (1006) a first fluorescent signal $S_1$ from the water sample, thus providing a baseline or reference point for future measurements. A first calibration solution is prepared (1008) to assist in determining the actual calibration slope, and a second fluorescent signal $S_2$ is measured (1010) from the first calibration solution. A calibration slope coefficient can then be determined (1012) based on the first signal $S_1$ and the second signal $S_2$.

In some cases the first calibration solution is prepared by increasing the concentration of fluorescent tracer within a portion of the water sample by a known amount. For example, in some embodiments preparing the first calibration solution includes preparing a spike solution that contains the water treatment product at a concentration of about P times the nominal concentration $C_0$ of the product in the water sample. In some cases the water treatment product also includes the fluorescent marker at a concentration of about P times the nominal concentration $C_f$ of the tracer within the water sample. In some embodiments the spike solution is mixed with the water sample at a ratio of about 1 part of the spike solution to about N parts of the water sample to create the first calibration solution. After measuring the second signal $S_2$ from the first calibration solution, the calibration slope coefficient, $K_m$, is calculated based on the first signal $S_1$ and the second signal $S_2$. In some embodiments, the spike solution contains the fluorescent tracer at a concentration of $P \times C_f$, the spike solution is mixed with the water sample in a ratio of about 1:N, and the slope coefficient $K_m$ is calculated as approximately equal to $$C_f \bigg/ \left( S_2 \left( \frac{N+1}{P} \right) - S_1 \left( \frac{N}{N+1} \right) \right).$$

It should be appreciated that a range of mixing ratios are possible for the first calibration solution. In some embodiments, N is between about 10 and about 500, while in some cases N is between about 90 and about 110. In some cases N is between about 5 and about 40. In some embodiments N is 99. In some embodiments P=N+1. In some embodiments P is 100, as is the case when P=N+1 and N is 99. Of course, other values for N and P are also possible, and the invention is not limited to the ranges and/or examples described herein.

Returning to FIG. 10, in addition to calculating (1012) the calibration slope coefficient, $K_m$, in some cases the method 1000 also includes determining a zero shift $Z_0$ for the calibration curve, representative of the amount of background fluorescence within the water sample apart from any fluorescence generated by the product. In some embodiments the zero shift is determined from a zero water sample having zero concentration of the water treatment product and/or fluorescent marker. For example, in some cases the zero water sample may be distilled water or tap water. In some cases, the zero water sample may be tap water acquired at the field location where the fluorescent measurements are being taken. In some cases the zero water sample may be acquired from a source of water that is normally mixed with the product as a carrier for use in an industrial water system.

After preparing (1014) the zero water sample, the method 1000 includes measuring (1016) a third fluorescent signal $S_3$ from the zero water sample and setting (1018) the zero shift equal to the third fluorescent signal $S_3$. The fluorometer can then be calibrated (1020) with the slope coefficient $K_m$ and the zero shift $Z_0$. For example, in some embodiments, a current concentration of a product, $C_c$, in a water sample can be determined according to the relationships $C_m=K_m \times (S_x-Z_0)$, and $C_c=C_m \times (C_0/C_f)$ as previously described herein.

Figure 11:
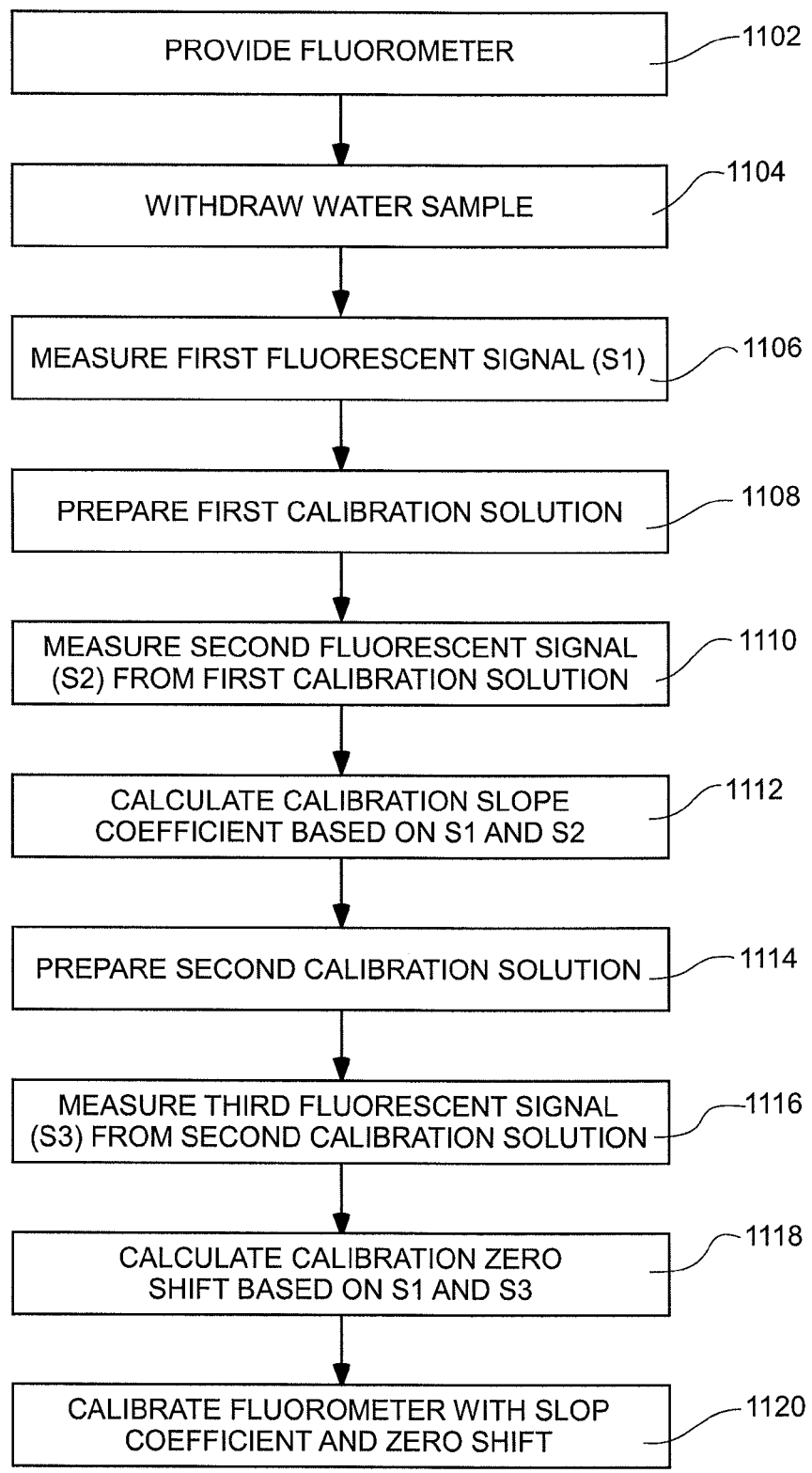
FIG. 11 is a flow diagram illustrating a method of calibrating a fluorometer according to some embodiments of the invention.

FIG. 11 is a flow diagram illustrating another method 1100 of calibrating a fluorometer according to some embodiments of the invention. The method 1100 includes several steps in common with those in the method 1000 of FIG. 10. For example, the method 1100 includes providing (1102) a fluorometer, withdrawing (1104) a water sample, and measuring (1106) a first fluorescent signal $S_1$ from the water sample. A first calibration solution is then prepared (1108), a second fluorescent measurement $S_2$ is measured (1110) from the first calibration solution, and the calibration slope coefficient can be calculated based on $S_1$ and $S_2$. In some embodiments the first calibration solution may be prepared in the same manner as described with respect to FIG. 10, although this is not required.

The method 1100 illustrated in FIG. 11 further includes preparing (1114) a second calibration solution, measuring (1116) a third fluorescent signal $S_3$ from the second calibration solution and calculating (1118) the zero shift based on $S_1$ and $S_3$. In some embodiments the second calibration solution is prepared from a portion of the water sample extracted from the industrial water system, and thus the zero shift can be calculated based upon the actual water within the industrial system, rather than with a zero water sample. Accordingly, calibrating (1120) a fluorometer with the slope coefficient and a zero shift acquired in such a way can more precisely account for the optical properties of the water in a specific on-site environment.

Figure 12A:
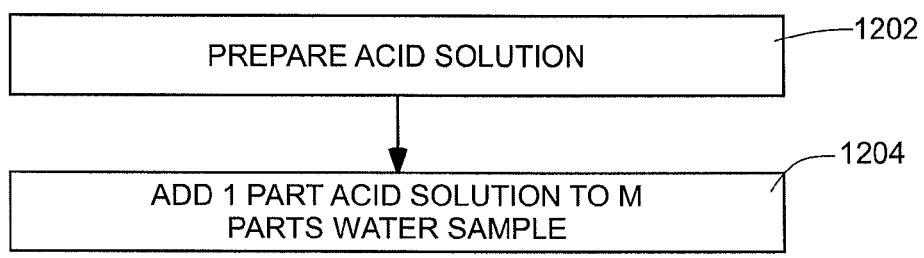
FIGS. 12A and 12B are flow diagrams illustrating methods of preparing a second calibration solution according to some embodiments of the invention.
Figure 12B:
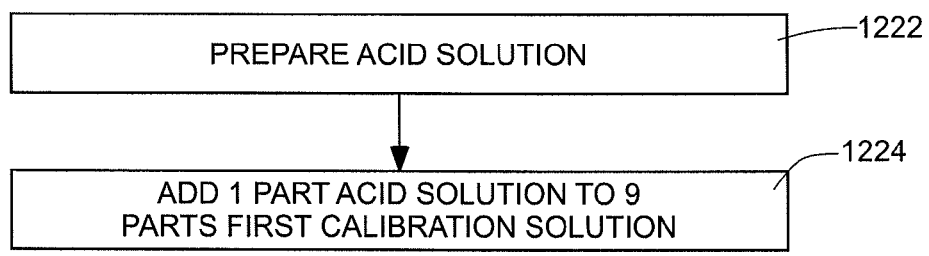

FIGS. 12A and 12B are flow diagrams illustrating, according to some embodiments of the invention, two methods of preparing (1114) the second calibration solution used in the method 1100 shown in FIG. 11. As shown in FIGS. 12A and 12B, in some embodiments the second calibration solution can be prepared using a portion of the water sample previously collected, or using a portion of the first calibration solution initially used to determine the calibration slope coefficient $K_m$. Of course, other methods of preparing the second calibration solution are also possible.

Referring to FIG. 12A, in some embodiments a method 1214A of preparing the second calibration solution includes preparing (1202) an acid solution and mixing (1204) the acid solution with a portion of the water sample. In some embodiments the acid solution comprises hydrochloric acid, although the invention is not limited to the use of any particular acid. In some embodiments about 1 part of the acid solution is added (1204) to about M parts of the water sample to create the second calibration solution, a third fluorescent signal $S_3$ is measured (1116 in FIG. 11) and the zero shift $Z_0$ is calculated (1118 in FIG. 11) as approximately equal to $$S_1 - S_3\left(\frac{M+1}{M}\right).$$

According to some embodiments, M is between about 9 and about 21. In some cases, $$\left(\frac{M+1}{2}\right) \leq Q \leq 2(M+1),$$

while in some embodiments Q=M+1. Of course, other values for M and Q are also possible, and the invention is not limited to the ranges and/or examples described herein.

FIG. 12B illustrates a method 1214B of preparing the second calibration solution based on a first calibration solution previously prepared (e.g., 1108 in FIG. 11) from the water sample. The method 1214B includes preparing (1222) an acid solution, and then mixing (1224) the acid solution with a portion of the first calibration solution. In some cases the acid solution contains from about 5% to about 30% acid. In some embodiments the acid solution comprises hydrochloric acid. In some cases the acid solution has a concentration of about 10% hydrochloric acid.

Returning to FIG. 12B, in some embodiments about 1 part of the acid solution is added (1224) to about 9 parts of the first calibration solution to create the second calibration solution. A third fluorescent signal $S_3$ can then be measured (e.g., 1116 in FIG. 11) and the zero shift $Z_0$ calculated (e.g., 1118 in FIG. 11) as approximately equal to $S_2-(S_3 \times 1.1)$. Of course, other values for the acid concentration and ratio of acid solution to first calibration solution are also possible, and the invention is not limited to the ranges and/or examples described herein. Once the zero shift $Z_0$ is determined, the fluorometer can be calibrated using the zero shift $Z_0$ and/or the calibration slope coefficient $K_m$ as previously described.

Figure 13A:
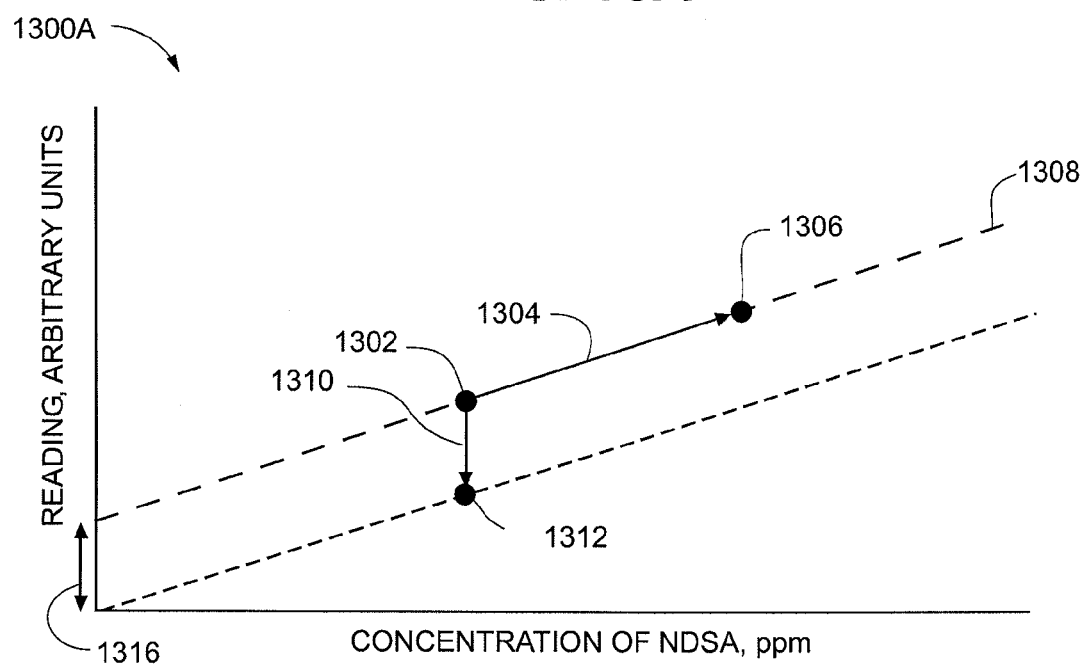
FIGS. 13A and 13B are plots illustrating hypothetical fluorescence measurements according to the methods of FIG. 11 and FIGS. 12A and 12B, respectively.

FIG. 13A is a plot 1300A illustrating a series of hypothetical fluorescence measurements taken while conducting the calibration methods of FIG. 11 and FIG. 12A. After withdrawing a water sample, a first fluorescent signal $S_1$ 1302 of the water sample is measured with a fluorometer. First and second calibration solutions are then prepared and successive measurements are taken in order to determine a calibration slope coefficient $K_m$ and a zero shift $Z_0$. As shown in FIGS. 11 and 12A, in some embodiments each of the first and the second calibration solutions can be prepared directly from a portion of the water sample, and the order of preparation may vary. As shown in FIG. 13A, the concentration of NDSA can be increased (shown by arrow 1304) by preparing a spike solution with an elevated concentration of NDSA, which is then used to "spike" a portion of the water sample, creating a first calibration solution. A second fluorescent measurement $S_2$ 1306 is taken from the first calibration solution, and the first and the second measurements $S_1$ 1302, $S_2$ 1306 can be used to determine the calibration slope coefficient $K_m$ to characterize the curve 1308. For example, in some cases the slope coefficient $K_m$ is calculated as approximately equal to $$C_f \bigg/ \left( S_2 \left( \frac{N+1}{P} \right) - S_1 \left( \frac{N}{N+1} \right) \right).$$

With continuing reference to FIG. 13A, an acid solution can then be added to a portion of the water sample in order to reduce or eliminate (shown by arrow 1310) a background fluorescence, thus creating a second calibration solution. A third fluorescence measurement $S_3$ 1312 can then be measured from the second calibration solution and the first and the third fluorescence measurements $S_1$ 1302, $S_3$ 1312 can then be used to determine the zero shift 1316 needed to correct for the background fluorescence effect. For example, the zero shift $Z_0$ may in some cases be calculated as approximately equal to $$S_1 - S_3 \left( \frac{M+1}{M} \right).$$

Future fluorometer readings can then be calibrated using the calibration slope coefficient $K_m$ and the zero shift $Z_0$.

Figure 13B:
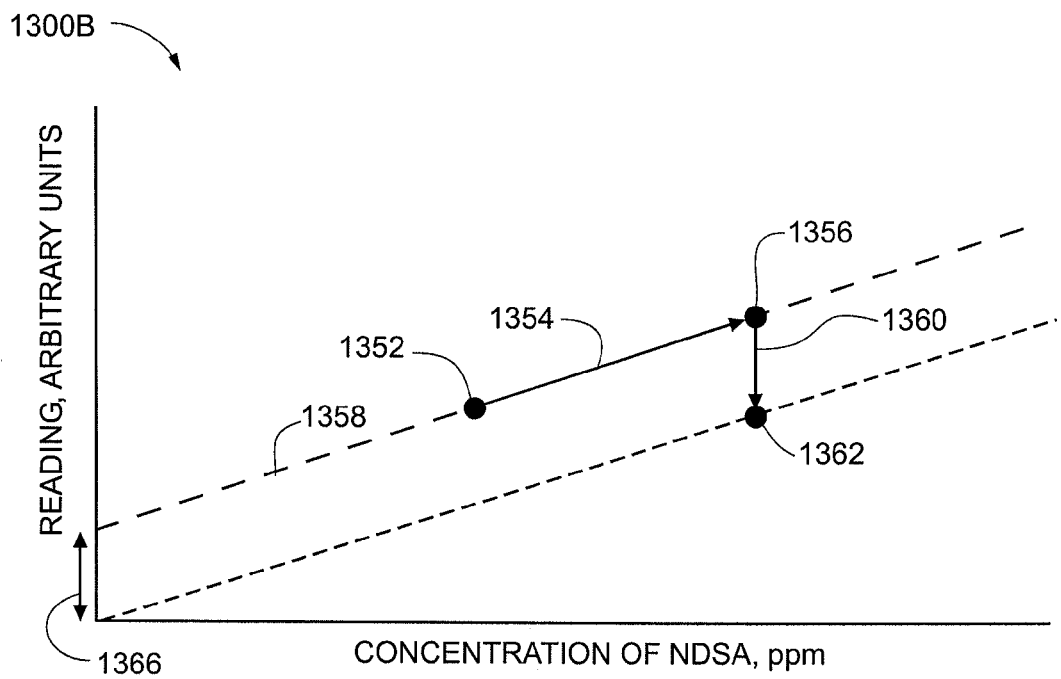

FIG. 13B is a plot 1300B illustrating a series of hypothetical fluorescence measurements taken while conducting the calibration methods of FIG. 11 and FIG. 12B. After withdrawing a water sample, a first fluorescent signal $S_1$ 1352 of the water sample is measured with a fluorometer. First and second calibration solutions are then prepared and successive measurements are taken in order to determine a calibration slope coefficient $K_m$ and a zero shift $Z_0$. As shown in FIGS. 11 and 12B, in some embodiments the first calibration solution is prepared directly from a portion of the water sample, and the second calibration solution is prepared from a portion of the first calibration solution. Referring to FIG. 13B, the concentration of NDSA can be increased (shown by arrow 1354) by preparing a spike solution with an elevated concentration of NDSA, which is then used to "spike" a portion of the water sample, creating a first calibration solution. A second fluorescent measurement $S_2$ 1356 is taken from the first calibration solution, and the first and the second measurements $S_1$ 1352, $S_2$ 1356 can be used to determine the calibration slope coefficient $K_m$ to characterize the curve 1358. For example, in some embodiments the slope coefficient, $K_m$, is calculated as approximately equal to $C_f/(S_2-S_1 \times 0.99)$.

With continuing reference to FIG. 13B, an acid solution can then be added to a portion of the first calibration solution in order to reduce or eliminate (shown by arrow 1310) a background fluorescence, thus creating a second calibration solution. A third fluorescence measurement $S_3$ 1312 can then be measured from the second calibration solution and the first and the third fluorescence measurements $S_1$ 1302, $S_3$ 1312 can be used to determine the zero shift 1316 needed to correct for the background fluorescence effect. For example, the zero shift $Z_0$ may in some cases be calculated as approximately equal to $S_2-(S_3 \times 1.1)$. Future fluorometer readings can then be calibrated using the calibration slope coefficient $K_m$ and the zero shift $Z_0$.

According to some embodiments of the invention, methods for calibrating a fluorometer advantageously utilize at least three points to increase the accuracy of the calibration, especially when compared with past two-point calibration schemes. For example, as discussed above, certain embodiments use at least two measurement points to characterize the slope of a calibration curve. A third point can be used with one of the first two measurement points to determine a zero offset for the calibration curve.

Figure 15:
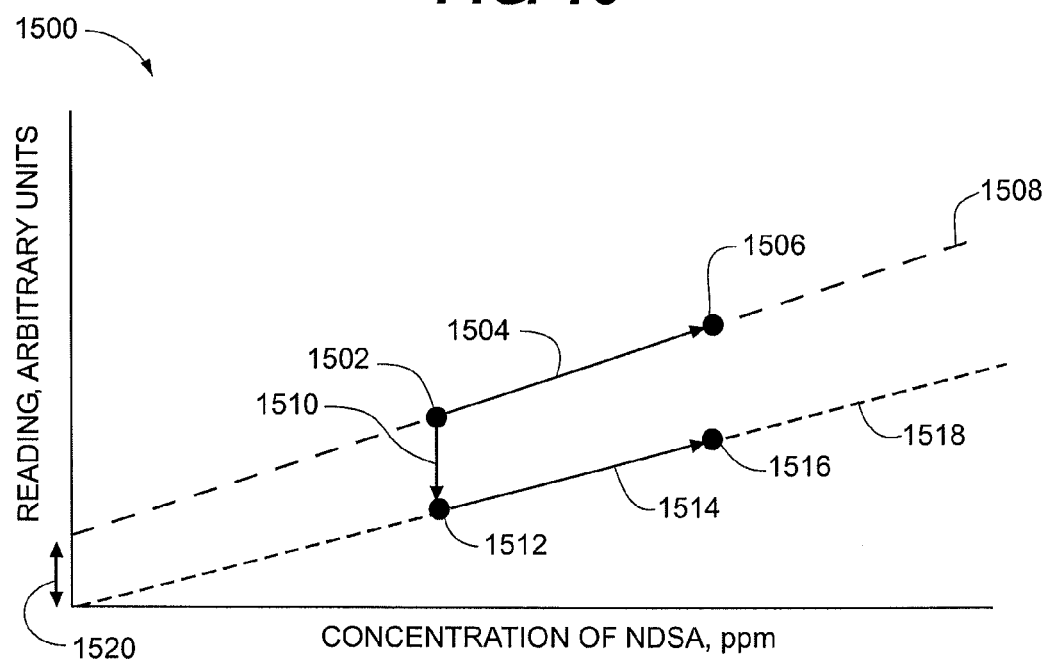
FIG. 15 is a plot illustrating hypothetical fluorescence measurements according to the method of FIG. 14.

Referring to FIGS. 14 and 15, some embodiments of the invention provide a four-point calibration method 1400. FIG. 14 is a flow diagram illustrating the method 1400, while FIG. 15 is a plot illustrating hypothetical fluorescence measurements taken while conducting the calibration method of FIG. 14. The method 1400 includes providing (1402) a fluorometer, such as one of those described herein or another, that is configured to measure a fluorescent signal from a fluorescent marker in a water sample and determine a concentration of a product in the water sample. After withdrawing (1404) a water sample, a first fluorescent signal $S_1$, 1502 is measured (1406) using the fluorometer. A concentration of NDSA within the sample water is increased (shown by arrow 1504) by preparing (1408) a first calibration solution. In some embodiments the first calibration solution is prepared by combining a first spike solution having the product in concentration of about $100 \times C_0$, and the fluorescent marker in concentration of about $100 \times C_f$ with a portion of the water sample. In some cases about 1 part of the first spike solution is added to about 99 parts of the water sample to prepare the first calibration solution. As shown in FIGS. 14 and 15, in some cases a second fluorescent signal S2 1506 is measured (1410) from the first calibration solution. In some embodiments the slope coefficient, $K_m$, which characterizes the curve 1508, is calculated as approximately equal to $C_f/(S_2-S_1 \times 0.99)$, although other variations are possible.

In some embodiments a second calibration solution is prepared (1414) by adding an acid solution with a portion of the water sample in order to reduce or eliminate (shown by arrow 1510) a background fluorescence in the water sample. For example, in some cases a second calibration solution can be prepared by first preparing an acid solution containing from about 5% to about 30% acid, and then adding about 1 part of the acid solution to about 9 parts of the water sample. A third fluorescent signal, $S_3$ 1512 is measured (1416) from the second calibration solution.

In some cases a third calibration solution is prepared (1418) by combining a second spike solution having the product in concentration of about $100 \times C_0$, and the fluorescent marker in concentration of about $100 \times C_f$ with a portion of the second calibration solution. In some cases about 1 part of the second spike solution is added to about 99 parts of the second calibration solution to prepare the third calibration solution. In some embodiments, the second spike solution is the same as the first spike solution. After preparing (1418) the third calibration solution, a fourth fluorescent signal $S_4$ 1516 is measured (1420) from the third calibration solution. In some embodiments the zero shift $Z_0$ 1520 can then be calculated based on the four fluorescent measurements and a background correction coefficient $B_z$. In some embodiments, the zero shift, $Z_0$, is calculated (1422) as approximately equal to $$\left( S_1 - \frac{(S_2 - S_1)(S_3 - B_z(S_4 - S_3))}{(S_4 - S_3)} \right).$$

As shown in FIG. 15, in some cases the slope of the calibration curve 1508 has a slightly different slope than the calibration curve 1518, believed to be due at least in part to the quenching 1510 of the background fluorescence prior to preparing the third calibration solution and measuring the fourth fluorescent measurement $S_4$ 1516. Accordingly, the four-point calibration method 1400 can in some cases provide an improved calibration method with higher accuracy than in past calibration methods. For example, as discussed above, the zero shift can be based on all four signal measurements S1, S2, S3, and S4. In some embodiments the zero shift is also based on the background correction coefficient. In some cases $B_z$ is between about 0.005 and 0.05. In some embodiments $B_z$ is about 0.0135.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. A method for calibrating a fluorometer comprising the steps of:
   a) providing a fluorometer configured to measure a fluorescent signal from a fluorescent marker in a sample of water from an industrial water system and determine from the fluorescent signal a concentration of a water treatment product in the sample of water, wherein a nominal concentration $C_0$ of the water treatment product corresponds to a nominal concentration $C_f$ of the fluorescent marker;
   b) withdrawing a water sample from the industrial water system;
   c) measuring a first fluorescent signal, $S_1$, from the water sample with the fluorometer;
   d) preparing a first calibration solution, comprising the steps of
      i) preparing a spike solution containing the water treatment product at a concentration of about $P \times C_0$ and the fluorescent marker at a concentration of about $P \times C_f$, and
      ii) adding about 1 part of the spike solution to about N parts of the water sample;
   e) measuring a second fluorescent signal, $S_2$, from the first calibration solution with the fluorometer;
   f) calculating a slope coefficient, $K_m$, approximately equal to $$C_f \Big/ \left( S_2\left(\frac{N+1}{P}\right) - S_1\left(\frac{N}{N+1}\right) \right);$$

g) measuring a third fluorescent signal, $S_3$, from a sample of a zero water sample;
   h) setting a zero shift, $Z_0$, equal to $S_3$; and
   i) calibrating the fluorometer with the slope coefficient and the zero shift.

2. The method of claim 1, wherein N is between 10 and 500.

3. The method of claim 1, wherein N is between 90 and 110.

4. The method of claim 1, wherein P=N+1.

5. The method of claim 1, wherein the water treatment product comprises the fluorescent marker.

6. The method of claim 5, wherein the fluorescent marker comprises NDSA.

7. The method of claim 1, wherein calibrating the fluorometer comprises calculating a current fluorescent marker concentration, $C_m$, approximately equal to $K_m \times (S_x - Z_0)$, wherein $S_x$ is a current fluorescent measurement.

8. The method of claim 7, further comprising calculating a current water treatment product concentration, $C_c$, in the industrial water system based on the current fluorescent marker concentration, $C_m$, wherein $C_c$, is approximately equal to $C_m \times (C_0/C_f)$.

9. A method for calibrating a fluorometer comprising the steps of:
   a) providing a fluorometer configured to measure a fluorescent signal from a fluorescent marker in a sample of water from an industrial water system and determine from the fluorescent signal a concentration of a water treatment product in the sample of water, wherein a nominal concentration $C_0$ of the water treatment product corresponds to a nominal concentration $C_f$ of the fluorescent marker;
   b) withdrawing a water sample from the industrial water system;
   c) measuring a first fluorescent signal, $S_1$, from the water sample with the fluorometer;
   d) preparing a first calibration solution, comprising the steps of
      i) preparing a spike solution containing the water treatment product at a concentration of about $P \times C_0$ and the fluorescent marker at a concentration of about $P \times C_f$, and
      ii) adding about 1 part of the spike solution to about N parts of the water sample;
   e) measuring a second fluorescent signal, $S_2$, from the first calibration solution with the fluorometer;
   f) calculating a slope coefficient, $K_m$, approximately equal to $$C_f \Big/ \left( S_2\left(\frac{N+1}{P}\right) - S_1\left(\frac{N}{N+1}\right) \right);$$

g) preparing a second calibration solution comprising the steps of
      i) preparing an acid solution containing about Q % acid, and
      ii) adding about 1 part of the acid solution to about M parts of the water sample;
   h) measuring a third fluorescent signal, $S_3$, from the second calibration solution with the fluorometer;
   i) calculating a zero shift, $Z_0$, approximately equal to $$S_1 - S_3\left(\frac{M+1}{M}\right);$$

and
   j) calibrating the fluorometer using the slope coefficient and the zero shift.

10. The method of claim 9, wherein N is between 10 and 500.

11. The method of claim 9, wherein N is between 90 and 110.

12. The method of claim 9, wherein N is between 5 and 40.

13. The method of claim 9, wherein M is between 9 and 21.

14. The method of claim 9, wherein P=N+1.

15. The method of claim 9, wherein $$\left(\frac{M+1}{2}\right) \leq Q \leq 2(M+1).$$

16. The method of claim 15, wherein Q=M+1.

17. The method of claim 9, wherein calibrating the fluorometer comprises calculating a current fluorescent marker concentration, $C_m$, approximately equal to $K_m \times (S_x - Z_0)$, wherein $S_x$ is a current fluorescent measurement.

18. The method of claim 17, further comprising calculating a current water treatment product concentration, $C_c$, in the industrial water system based on the current fluorescent marker concentration, $C_m$, wherein $C_c$ is approximately equal to $C_m \times (C_0/C_f)$.

19. The method of claim 9, wherein the water sample has a volume that is two or more times greater than a minimum volume needed to take a fluorometric reading with the fluorometer.

20. The method of claim 9, wherein the fluorescent marker comprises NDSA.

21. The method of claim 9, wherein the acid comprises hydrochloric acid.

22. A method for calibrating a fluorometer comprising the steps of:
  a) providing a fluorometer configured to measure a fluorescent signal from a fluorescent marker in a sample of water from an industrial water system and determine from the fluorescent signal a concentration of a water treatment product in the sample of water, wherein a nominal concentration $C_0$ of the water treatment product corresponds to a nominal concentration $C_f$ of the fluorescent marker;
  b) withdrawing a water sample from the industrial water system;
  c) measuring a first fluorescent signal, $S_1$, from the water sample with the fluorometer;
  d) preparing a first calibration solution, comprising the steps of
    i) preparing a spike solution containing the water treatment product in a concentration of approximately $100 \times C_0$ and the fluorescent marker in a concentration of about $100 \times C_f$, and
    ii) adding about 1 part of the spike solution to about 99 parts of the water sample;
  e) measuring a second fluorescent signal, $S_2$, from the first calibration solution with the fluorometer;
  f) calculating a slope coefficient, $K_m$, approximately equal to $C_f/(S_2 - S_1 \times 0.99)$;
  g) preparing a second calibration solution, comprising the steps of
    i) preparing an acid solution containing from about 5% to about 30% acid, and
    ii) adding about 1 part of the acid solution to about 9 parts of the first calibration solution;
  h) measuring a third fluorescent signal, $S_3$, from the second calibration solution;
  i) calculating a zero shift, $Z_0$, approximately equal to $S_2 - (S_3 \times 1.1)$; and
  j) calibrating the fluorometer with the slope coefficient and the zero shift.

23. The method of claim 22, wherein calibrating the fluorometer comprises calculating a current fluorescent marker concentration, $C_m$, approximately equal to $K_m \times (S_x - Z_0)$, wherein $S_x$ is a current fluorescent measurement.

24. The method of claim 23, further comprising calculating a current concentration of the water treatment product, $C_c$, in the industrial water system based on the current fluorescent marker concentration, $C_m$, wherein $C_c$ is approximately equal to $C_m \times (C_0/C_f)$.

25. The method of claim 22, wherein the water sample has a volume that is two or more times greater than a minimum volume needed to take a fluorometric reading with the fluorometer.

26. The method of claim 22, wherein the fluorescent marker comprises NDSA.

27. The method of claim 26, wherein a nominal concentration of the NDSA is from about 0.1 ppm to about 3 ppm.

28. The method of claim 27, wherein the nominal concentration of the NDSA is about 0.5 ppm.

29. The method of claim 22, wherein the acid comprises hydrochloric acid.

30. The method of claim 29, wherein the acid solution has a concentration of the hydrochloric acid of about 10%.

31. A method for calibrating a fluorometer comprising the steps of:
  a) providing a fluorometer configured to measure a fluorescent signal from a fluorescent marker in a sample of water from an industrial water system and determine from the fluorescent signal a concentration of a water treatment product in the sample of water wherein a nominal concentration $C_0$ of the water treatment product corresponds to a nominal concentration $C_f$ of the fluorescent marker;
  b) withdrawing a water sample from the industrial water system;
  c) measuring a first fluorescent signal, $S_1$, from the water sample with the fluorometer;
  d) preparing a first calibration solution, comprising the steps of
    i) preparing a first spike solution containing the water treatment product in a concentration of approximately $100 \times C_0$ and the fluorescent marker in a concentration of about $100 \times C_f$, and
    ii) adding about 1 part of the first spike solution to about 99 parts of the water sample;
  e) measuring a second fluorescent signal, $S_2$, from the first calibration solution with the fluorometer;
  f) preparing a second calibration solution, comprising the steps of
    i) preparing an acid solution containing from about 5% to about 30% acid, and
    ii) adding about 1 part of the acid solution to about 9 parts of the water sample;
  g) measuring a third fluorescent signal, $S_3$, from the second calibration solution
  h) preparing a third calibration solution, comprising the steps of
    i) preparing a second spike solution containing the water treatment product in concentration of approximately $100 \times C_0$ and the fluorescent marker in a concentration of about $100 \times C_f$; and
    ii) adding about 1 part of the spike solution to about 99 parts of the second calibration solution;

i) measuring a fourth fluorescent signal, $S_4$, from the third calibration solution with the fluorometer;

j) calculating a slope coefficient, $K_m$, approximately equal to $C_f/(S_2-S_1 \times 0.99)$;

k) calculating a zero shift, $Z_0$, approximately equal to $$\left(S_1 - \frac{(S_2 - S_1)(S_3 - B_z(S_4 - S_3))}{(S_4 - S_3)}\right),$$

wherein $B_z$ is a background correction coefficient approximately between about 0.005 and about 0.05; and l) calibrating the fluorometer with the slope coefficient and the zero shift.

32. The method of claim 31, wherein calibrating the fluorometer comprises calculating a current fluorescent marker concentration, $C_m$, in the industrial water system approximately equal to $K_m \times (S_x - Z_0)$, wherein $S_x$ is a current fluorescent measurement.

33. The method of claim 32, further comprising calculating a current water treatment product concentration, $C_c$, of the water treatment product based on the current fluorescent marker concentration, $C_m$, wherein $C_c$ is approximately equal to $C_m \times (C_0/C_f)$.

34. The method of claim 31, wherein the water sample has a volume that is two or more times greater than a minimum volume needed to take a fluorometric reading with the fluorometer.

35. The method of claim 31, wherein the fluorescent marker comprises NDSA.

36. The method of claim 35, wherein a nominal concentration of the NDSA is from about 0.1 ppm to about 3 ppm.

37. The method of claim 35, wherein a nominal concentration of the NDSA is about 0.5 ppm.

38. The method of claim 31, wherein the acid comprises hydrochloric acid.

39. The method of claim 38, wherein a concentration of the hydrochloric acid is about 10%.

40. The method of claim 31, wherein the background correction coefficient, $B_z$, is about 0.0135.

\* \* \* \* \*